US008268799B2

(12) United States Patent
Nakayama et al.

(10) Patent No.: US 8,268,799 B2
(45) Date of Patent: Sep. 18, 2012

(54) COMPOSITIONS AND METHODS FOR INHIBITING EXPRESSION OF THE HAMP GENE

(75) Inventors: Tomoko Nakayama, Cambridge, MA (US); Anke Geick, Bayreuth (DE); Pamela Tan, Kulmbach (DE); Herbert Y. Lin, Watertown, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/184,087

(22) Filed: Jul. 15, 2011

(65) Prior Publication Data
US 2011/0269823 A1  Nov. 3, 2011

Related U.S. Application Data

(62) Division of application No. 12/757,497, filed on Apr. 9, 2010, now Pat. No. 8,163,711, which is a division of application No. 11/859,288, filed on Sep. 21, 2007, now abandoned.

(60) Provisional application No. 60/846,266, filed on Sep. 21, 2006, provisional application No. 60/870,253, filed on Dec. 15, 2006.

(51) Int. Cl.
*A61K 31/70* (2006.01)
*C07H 21/02* (2006.01)
*C07H 21/04* (2006.01)
(52) U.S. Cl. ............... 514/44 A; 536/24.1; 536/24.5
(58) Field of Classification Search .............. 514/44
See application file for complete search history.

(56) References Cited

U.S. PATENT DOCUMENTS

| 7,427,605 | B2 | 9/2008 | Davis et al. |
| 7,718,629 | B2 | 5/2010 | Bumcrot et al. |
| 2003/0143732 | A1 | 7/2003 | Fosnaugh et al. |
| 2003/0170891 | A1 | 9/2003 | McSwiggen |
| 2004/0259247 | A1 | 12/2004 | Tuschl et al. |
| 2006/0263435 | A1 | 11/2006 | Davis et al. |
| 2007/0004664 | A1 | 1/2007 | McSwiggen et al. |
| 2007/0031844 | A1 | 2/2007 | Khvorova et al. |
| 2007/0281899 | A1 | 12/2007 | Bumcrot et al. |
| 2009/0149403 | A1 | 6/2009 | MacLachlan |
| 2011/0015250 | A1 | 1/2011 | Bumcrot et al. |

FOREIGN PATENT DOCUMENTS

WO  WO 2004/080406  9/2004
WO  WO 2004/090108  10/2004

OTHER PUBLICATIONS

Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.

(Continued)

*Primary Examiner* — Terra Cotta Gibbs
(74) *Attorney, Agent, or Firm* — Fenwick & West LLP

(57) ABSTRACT

The invention relates to a double-stranded ribonucleic acid (dsRNA) for inhibiting the expression of the HAMP gene (HAMP gene), comprising an antisense strand having a nucleotide sequence which is less that 30 nucleotides in length, generally 19-25 nucleotides in length, and which is substantially complementary to at least a part of the HAMP gene. The invention also relates to a pharmaceutical composition comprising the dsRNA together with a pharmaceutically acceptable carrier; methods for treating diseases caused by HAMP gene expression and the expression of the HAMP gene using the pharmaceutical composition.

24 Claims, 9 Drawing Sheets

OTHER PUBLICATIONS

Elbashir, S., et al., "Analysis of gene function in somatic mammalian cells using small interfering RNAs," Methods, 2002, pp. 199-213, vol. 26.

Elbashir, S., et al., "Duplexes of 21-nucleotide RNAs mediate RNA interference in mammalian cell culture," Nature, May 24, 2001, p. 494-498, vol. 411.

Elbashir, S., et al., "Functional Anatomy of siRNAs for Mediating Efficient RNAi in Drosophila Melanogaster Embryo Lysate", The EMBO Journal, 2001, pp. 6877-6888, vol. 20, No. 23.

Elbashir, S., et al., "RNA Interference is Mediated by 21-and 22 Nucleotide RNAs," Genes & Development, 2001, pp. 188-200, vol. 15.

Fire, A., "RNA-triggered Gene Silencing," Trends in Genetics, Sep. 1999, pp. 358-363, vol. 15, No. 9.

Fire, A., et al., "Potent and Specific Genetic Interference by Double Stranded RNA in Caenorhabditis elegans," Nature, Feb. 19, 1998, pp. 806-811, vol. 391.

Reynolds, et al. (2004) "Rational siRNA design for RNA interference," Nature Biotechnology, vol. 22, No. 3, pp. 326-330.

Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.

Rose, S., et al., "Functional polarity is introduced by Dicer processing of short substrate RNAs," Nucleic Acids Research, 2005, pp. 4140-4156, vol. 33, No. 13.

Tuschl, T., "Functional genomics: RNA sets the standard," Nature, Jan. 16, 2003, vol. 421, No. 6920, pp. 220-221.

Tuschl T., "RNA Interference and Small Interfering RNAs" Chembiochem, 2001, pp. 239-245, vol. 2.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., "Mammalian RNA Interference," RNAi, A Guide to Gene Silencing, Chapter 13, G.J. Hannon (ed,), 2003, pp. 265-295.

Tuschl, T., et al., "Targeted mRNA Degradation by Double-Stranded RNA in Vitro," Genes & Development, 1999, pp. 3191-3197, vol. 13.

Tuschl, T., "Expanding small RNA interference," Nature Biotechnology, May 2002, pp. 446-448, vol. 20.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

Weil, et al (2002) "Targeting the Kinesin Eg5 to Monitor siRNA Transfection in Mammalian Cells," *Biotechniques* 33(6):1244-1248.

Zimmerman, et al. (2006) "RNAi-mediated gene silencing in non-human primates," *Nature*, vol. 441, May 4: 111-114.

GenBank Accession No. NM_032541.1 (Oct. 22, 2011), NCBI Sequence Viewer, [online] [Retrieved on Nov. 18, 2011] Retrieved from the internet <URL:http://www.ncbi.nlm.nih.gov/nuccore/NM_032541.1>.

Office Action for Canadian Patent Application No.: CA 2,663,581, mailed on May 14, 2012, 2 Pages.

COMPOSITIONS AND METHODS FOR INHIBITING EXPRESSION OF THE HAMP GENE

CROSS-REFERENCE TO RELATED APPLICATIONS

This application is a divisional of U.S. application Ser. No. 12/757,497, filed Apr. 9, 2010 (pending); which is a divisional of U.S. application Ser. No. 11/859,288, filed Sep. 21, 2007 (abandoned) which all claim the benefit of U.S. Provisional Application No. 60/846,266, filed Sep. 21, 2006; and U.S. Provisional Application No. 60/870,253, filed Dec. 15, 2006. The entire contents of these applications are hereby incorporated by reference in the present application.

FIELD OF THE INVENTION

This invention relates to double-stranded ribonucleic acid (dsRNA), and its use in mediating RNA interference to inhibit the expression of the HAMP gene and the use of the dsRNA to treat pathological processes which can be mediated by down regulating HAMP, such as anemia and other diseases associated with lowered iron levels.

BACKGROUND OF THE INVENTION

The discovery of the hepcidin peptide and characterization of its gene, HAMP,[4] has led to the revision of previous models for the regulation of iron homeostasis and the realisation that the liver plays a key role in determining iron absorption from the gut and iron release from recycling and storage sites. Perhaps the most striking example has been to change the pathogenic model of HFE-related hereditary haemochromatosis from the crypt-programming model centered on the duodenal absorptive enterocyte to the hepcidin model centered on the hepatocyte.[5,6] In summary, the hepcidin model proposes that the rate of iron efflux into the plasma depends primarily on the plasma level of hepcidin; when iron levels are high the synthesis of hepcidin increases and the release of iron from enterocytes and macrophages is diminished. Conversely when iron stores drop, the synthesis of hepcidin is down-regulated and these cells release more iron.

In order to describe the postulated major role of hepcidin it is necessary to understand the function of ferroportin, a protein first characterised in 2000. Ferroportin is the major iron export protein located on the cell surface of enterocytes, macrophages and hepatocytes, the main cells capable of releasing iron into plasma for transport by transferrin.[7]

The major iron recycling pathway is centered on the degradation of senescent red cells by reticuloendothelial macrophages located in bone marrow, hepatic Kupffer cells and spleen. The exit of iron from these macrophages is controlled by ferroportin. The role of the hepatocyte is central to the action of ferroportin, because the hepatocyte is proposed to sense body iron status and either release or down-regulate hepcidin, which then interacts with ferroportin to modulate the release of cellular iron. Hepcidin directly binds to ferroportin and decreases its functional activity by causing it to be internalized from the cell surface and degraded.[8]

Increased hepcidin synthesis is thought to mediate iron metabolism in two clinically important circumstances, shown schematically in FIG. 1. In individuals who do not harbour mutations causing haemochromatosis, the hepatocyte is thought to react to either an increase in iron saturation of transferrin or to increased iron stores in hepatocytes themselves, by inducing the synthesis of hepcidin by an as yet unknown mechanism. Thus the physiological response to iron overload under normal circumstances would be the hepcidin mediated shut down of iron absorption (enterocyte), recycling (macrophage) and storage (hepatocyte).

The synthesis and release of hepcidin is also rapidly mediated by bacterial lipopolysaccharide and cytokine release, especially interleukin-6 Thus the hepcidin gene is an acute-phase responsive gene which is overexpressed in response to inflammation. Cytokine mediated induction of hepcidin caused by inflammation or infection is now thought to be responsible for the anaemia of chronic disease, where iron is retained by the key cells that normally provide it, namely enterocytes, macrophages and hepatocytes. Retention of iron leads to the hallmark features of the anaemia of chronic disease, low transferrin saturation, iron-restricted erythropoeisis and mild to moderate anaemia.[9] The nature of the hepcidin receptor is presently unknown, however an exciting future prospect may be the development of agents to block the receptor with the aim of treating the anaemia of chronic disease, a common often intractable clinical problem.

Down-regulation of hepcidin synthesis results in increased iron release, which arises in the two situations shown schematically in FIG. 2. The main causes of non-HFE haemochromatosis are mutations in either ferroportin, transferrin receptor 2, hepcidin or hemojuvelin genes. Classical HFE haemochromatosis, and all types of non-HFE haemochromatosis thus far studied with the exception of ferroportin related haemochromatosis, are characterised by inappropriate hepcidin deficiency. In these circumstances, hepatocytes become iron loaded, because their uptake of transferrin bound iron from the circulation is assumed to exceed that of ferroportin mediated export. Hepcidin deficiency causes increased ferroportin mediated iron export, resulting in increased enterocyte absorption of iron and perhaps quantitatively more important, enhanced export of recycled iron onto plasma transferrin by macrophages. Hepcidin is also suppressed in thalassaemic syndromes, both β thalassaemia major and intermedia and congenital dyserythropoetic anaemic type 1, where iron absorption is inappropriately stimulated despite the presence of massive iron overload.[10]

As shown in FIG. 2, anaemia and hypoxia both trigger a decrease in hepcidin levels. These discoveries were made in animal models and need to be further studied to show they are applicable in humans. Two animal models of anaemia in mice were used to demonstrate a dramatic decrease in hepcidin synthesis where anaemia was provoked either by excessive bleeding or haemolysis.[11] This is postulated to permit the rapid mobilisation of iron from macrophages and enterocytes necessary to allow for the increased erythropoietic activity triggered by erythropoietin release. The same study showed down-regulation of hepcidin synthesis can be triggered by hypoxia alone, and mice housed in hypobaric hypoxia chambers simulating an altitude of 5,500 m also showed a rapid decrease in hepcidin.

In summary, hepcidin provides a unifying hypothesis to explain the behaviour of iron in two diverse but common clinical conditions, the anaemia of chronic disease and both HFE and non-HFE haemochromatosis. The pathophysiology of hepcidin has been sufficiently elucidated to offer promise of therapeutic intervention in both of these situations. Administering either hepcidin or an agonist could treat haemochromatosis, where the secretion of hepcidin is abnormally low.

1. Park C H, Valore E V, Waring A J, Ganz T. Hepcidin, a urinary antimicrobial peptide synthesized in the liver. J Biol Chem. 2001; 276:7806-10.
2. Pigeon C, Ilyin G, Courselaud B, et al. A new mouse liver-specific gene, encoding a protein homologous to human antimicrobial peptide hepcidin, is overexpressed during iron overload. J Biol Chem. 2001; 276:7811-9.

3. Ganz T. Hepcidin, a key regulator of iron metabolism and mediator of anemia of inflammation. Blood. 2003; 102: 783-8.

4. Roetto A, Papanikolaou G, Politou M, et al. Mutant antimicrobial peptide hepcidin is associated with severe juvenile hemochromatosis. Nat Genet. 2003; 33:21-2.

5. Fleming R E. Advances in understanding the molecular basis for the regulation of dietary iron absorption. Curr Opin Gastroenterol. 2005; 21:201-6.

6. Pietrangelo A. Hereditary hemochromatosis—a new look at an old disease. N Engl J Med. 2004; 350:2383-97.

7. Donovan A, Brownlie A, Zhou Y, et al. Positional cloning of zebrafish ferroportin 1 identifies a conserved vertebrate iron exporter. Nature. 2000; 403:776-81.

8. Nemeth E, Tuttle M S, Powelson J, et al. Hepcidin regulates cellular iron efflux by binding to ferroportin and inducing its internalization. Science. 2004; 306:2090-3.

9. Weiss G, Goodnough L T. Anemia of chronic disease. N Engl J Med. 2005; 352:1011-23.

10. Papanikolaou G, Tzilianos M, Christakis J I, et al. Hepcidin in iron overload disorders. Blood. 2005; 105:4103-5.

11. Nicolas G, Chauvet C, Viatte L, et al. The gene encoding the iron regulatory peptide hepcidin is regulated by anemia, hypoxia, and inflammation. J Clin Invest. 2002; 110: 1037-44.

The anemia of inflammation, commonly observed in patients with chronic infections, malignancy, trauma, and inflammatory disorders, is a well-known clinical entity. Until recently, little was understood about its pathogenesis. It now appears that the inflammatory cytokine IL-6 induces production of hepcidin, an iron-regulatory hormone that may be responsible for most or all of the features of this disorder. (Andrews N C. *J Clin Invest.* 2004 May 1; 113 (9): 1251-1253). As such, down regulation of hepcidin in anemic patients will lead to a reduction in inflammation associated with such anemia.

Recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

Despite significant advances in the field of RNAi and advances in the treatment of pathological processes which can be mediated by down regulating HAMP gene expression, there remains a need for agents that can inhibit HAMP gene expression and that can treat diseases associated with HAMP gene expression such as anemia and other diseases associated with lowered iron levels.

SUMMARY OF THE INVENTION

The invention provides a solution to the problem of treating diseases that can be modulated by down regulating the protein hepcidin gene/protein (HAMP) by using double-stranded ribonucleic acid (dsRNA) to silence HAMP expression.

The invention provides double-stranded ribonucleic acid (dsRNA), as well as compositions and methods for inhibiting the expression of the HAMP gene in a cell or mammal using such dsRNA. The invention also provides compositions and methods for treating pathological conditions that can be modulated by down regulating the expression of the HAMP gene, such as anemia and other diseases associated with lowered iron levels. The dsRNA of the invention comprises an RNA strand (the antisense strand) having a region which is less than 30 nucleotides in length, generally 19-24 nucleotides in length, and is substantially complementary to at least part of an mRNA transcript of the HAMP gene.

In one embodiment, the invention provides double-stranded ribonucleic acid (dsRNA) molecules for inhibiting the expression of the HAMP gene. The dsRNA comprises at least two sequences that are complementary to each other. The dsRNA comprises a sense strand comprising a first sequence and an antisense strand comprising a second sequence. The antisense strand comprises a nucleotide sequence which is substantially complementary to at least part of an mRNA encoding HAMP, and the region of complementarity is less than 30 nucleotides in length, generally 19-24 nucleotides in length. The dsRNA, upon contacting with a cell expressing the HAMP, inhibits the expression of the HAMP gene by at least 40%.

For example, the dsRNA molecules of the invention can be comprised of a first sequence of the dsRNA that is selected from the group consisting of the sense sequences of Tables 1 or 3 and the second sequence is selected from the group consisting of the antisense sequences of Tables 1 or 3. The dsRNA molecules of the invention can be comprised of naturally occurring nucleotides or can be comprised of at least one modified nucleotide, such as a 2'-O-methyl modified nucleotide, a nucleotide comprising a 5'-phosphorothioate group, and a terminal nucleotide linked to a cholesteryl derivative. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such modified sequence will be based on a first sequence of said dsRNA selected from the group consisting of the sense sequences of Tables 1 or 3 and a second sequence selected from the group consisting of the antisense sequences of Tables 1 or 3.

In another embodiment, the invention provides a cell comprising one of the dsRNAs of the invention. The cell is generally a mammalian cell, such as a human cell.

In another embodiment, the invention provides a pharmaceutical composition for inhibiting the expression of the HAMP gene in an organism, generally a human subject, comprising one or more of the dsRNA of the invention and a pharmaceutically acceptable carrier or delivery vehicle. Preferable the carrier or delivery vehicle will be one that selectively targets the siRNA to the liver.

In another embodiment, the invention provides a method for inhibiting the expression of the HAMP gene in a cell, comprising the following steps:

(a) introducing into the cell a double-stranded ribonucleic acid (dsRNA), wherein the dsRNA comprises at least two sequences that are complementary to each other. The dsRNA comprises a sense strand comprising a first sequence and an antisense strand comprising a second sequence. The antisense strand comprises a region of complementarity which is substantially complementary to at least a part of a mRNA encoding HAMP, and wherein the region of complementarity is less than 30 nucleotides in length, generally 19-24 nucleotides in length, and wherein the dsRNA, upon contact with a cell expressing the HAMP, inhibits expression of the HAMP gene by at least 40%; and (b) maintaining the cell produced in step (a) for a time sufficient to obtain degradation of the mRNA transcript of the HAMP gene, thereby inhibiting expression of the HAMP gene in the cell.

In another embodiment, the invention provides methods for treating, preventing or managing pathological processes which can be mediated by down regulating HAMP gene expression, e.g. anemia and other diseases associated with lowered iron levels., comprising administering to a patient in need of such treatment, prevention or management a therapeutically or prophylactically effective amount of one or more of the dsRNAs of the invention.

In another embodiment, the invention provides vectors for inhibiting the expression of the HAMP gene in a cell, comprising a regulatory sequence operably linked to a nucleotide sequence that encodes at least one strand of one of the dsRNA of the invention.

In another embodiment, the invention provides a cell comprising a vector for inhibiting the expression of the HAMP gene in a cell. The vector comprises a regulatory sequence operably linked to a nucleotide sequence that encodes at least one strand of one of the dsRNA of the invention.

DETAILED DESCRIPTION OF THE INVENTION

Figure 1:
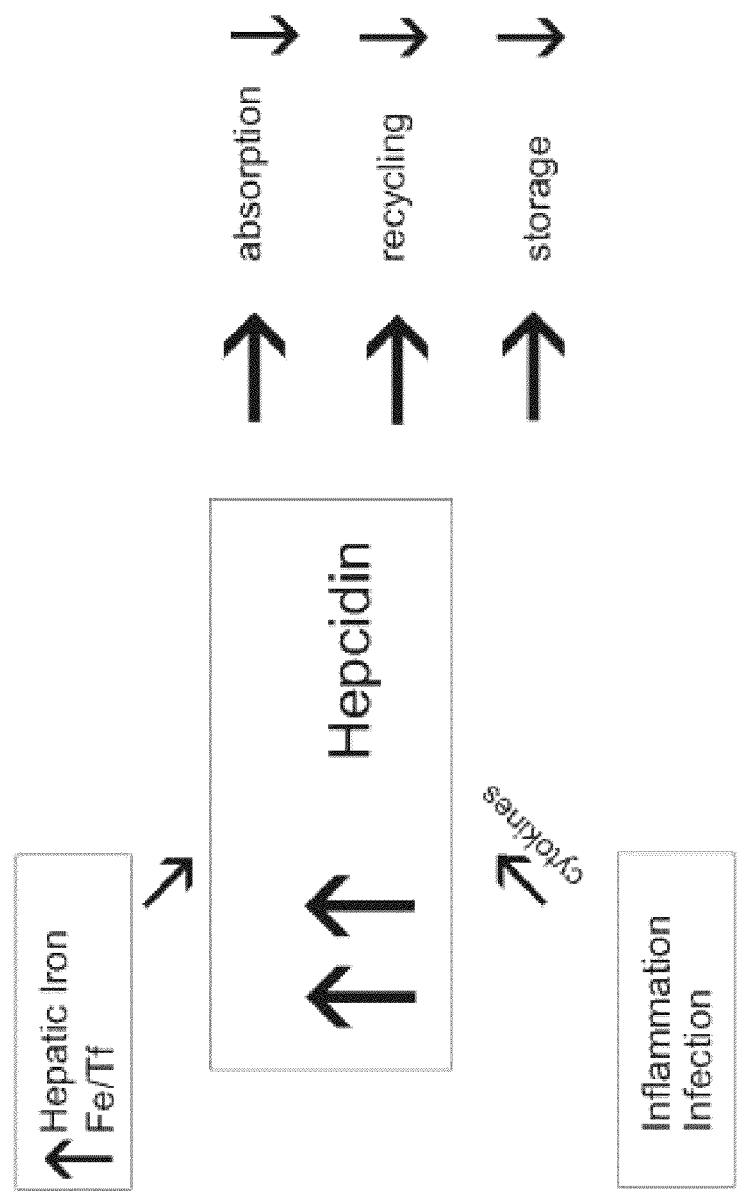
FIG. 1 is a schematic diagram illustrating induction of liver hepcidin synthesis, which decreases iron export from absorptive cells (enterocytes), recycling cells (macrophages) and storage cells (hepatocytes).
Figure 2:
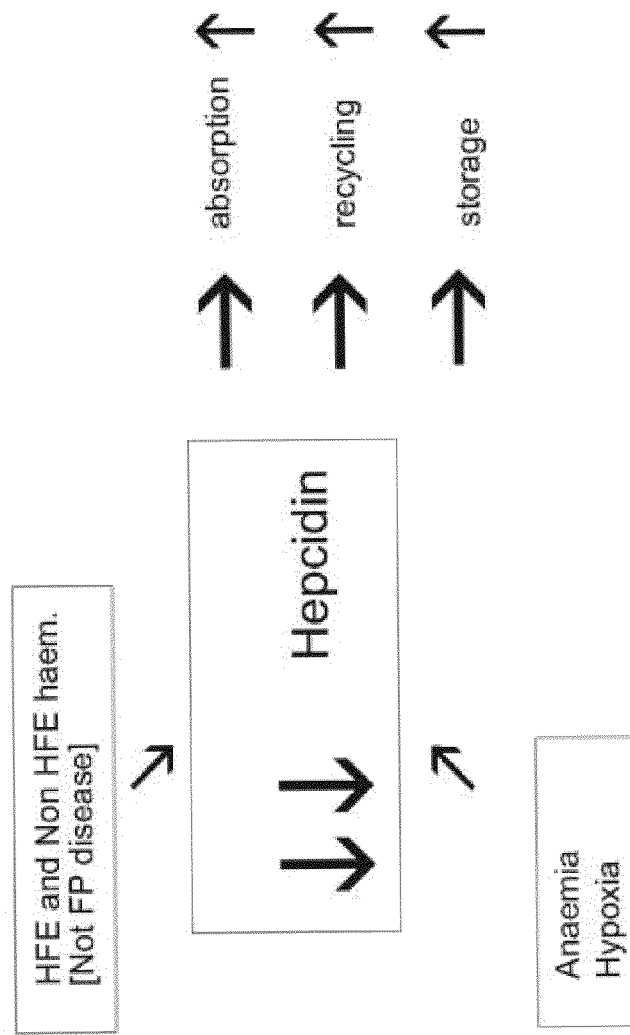
FIG. 2 is a schematic diagram illustrating that down-regulation of liver hepcidin synthesis increases iron export from absorptive cells (enterocytes), recycling cells (macrophages) and storage cells (hepatocytes). The box labelled 'HFE- and Non-HFE haemochromatosis. (not FP disease)' refers to HFE- and non-HFE haemochromatosis with the sole exception of ferroportin disease.

The invention provides a solution to the problem of treating diseases that can be modulated by the down regulation of the HAMP gene, by using double-stranded ribonucleic acid (dsRNA) to silence the HAMP gene thus providing treatment for diseases such as anemia and other diseases associated with lowered iron levels.

The invention provides double-stranded ribonucleic acid (dsRNA), as well as compositions and methods for inhibiting the expression of the HAMP gene in a cell or mammal using the dsRNA. The invention also provides compositions and methods for treating pathological conditions and diseases that can be modulated by down regulating the expression of the HAMP gene. dsRNA directs the sequence-specific degradation of mRNA through a process known as RNA interference (RNAi).

The dsRNA of the invention comprises an RNA strand (the antisense strand) having a region which is less than 30 nucleotides in length, generally 19-24 nucleotides in length, and is substantially complementary to at least part of an mRNA transcript of the HAMP gene. The use of these dsRNAs enables the targeted degradation of an mRNA that is involved in sodium transport. Using cell-based and animal assays, the present inventors have demonstrated that very low dosages of these dsRNA can specifically and efficiently mediate RNAi, resulting in significant inhibition of expression of the HAMP gene. Thus, the methods and compositions of the invention comprising these dsRNAs are useful for treating pathological processes which can be mediated by down regulating HAMP, such as in the treatment of anemia and other diseases associated with lowered iron levels.

The following detailed description discloses how to make and use the dsRNA and compositions containing dsRNA to inhibit the expression of the target HAMP gene, as well as compositions and methods for treating diseases that can be modulated by down regulating the expression of HAMP, such as anemia and other diseases associated with lowered iron levels. The pharmaceutical compositions of the invention comprise a dsRNA having an antisense strand comprising a region of complementarity which is less than 30 nucleotides in length, generally 19-24 nucleotides in length, and is substantially complementary to at least part of an RNA transcript of the HAMP gene, together with a pharmaceutically acceptable carrier.

Accordingly, certain aspects of the invention provide pharmaceutical compositions comprising the dsRNA of the invention together with a pharmaceutically acceptable carrier, methods of using the compositions to inhibit expression of the HAMP gene, and methods of using the pharmaceutical compositions to treat diseases that can be modulated by down regulating the expression of HAMP.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, "HAMP" refers to the hepcidin gene or protein (also known as LEAP). mRNA sequences to HAMP are provided as human: Genbank accession NM_021175.2.

As used herein, "target sequence" refers to a contiguous portion of the nucleotide sequence of an mRNA molecule formed during the transcription of the HAMP gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding HAMP). For example, a polynucleotide is complementary to at least a part of a HAMP mRNA if the sequence is substantially complementary to a non-interrupted portion of a mRNA encoding HAMP.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where separate RNA molecules, such dsRNA are often referred to in the literature as siRNA ("short interfering RNA"). Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop", "short hairpin RNA" or "shRNA". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. In addition, as used in this specification, "dsRNA" may include chemical modifications to ribonucleotides, including substantial modifications at multiple nucleotides and including all types of modifications disclosed herein or known in the art. Any such modifications, as used in an siRNA type molecule, are encompassed by "dsRNA" for the purposes of this specification and claims.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule. For clarity, chemical caps or non-nucleotide chemical moieties conjugated to the 3' end or 5' end of an siRNA are not considered in determining whether an siRNA has an overhang or is blunt ended.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of", in as far as they refer to the HAMP gene, herein refer to the at least partial suppression of the expression of the HAMP gene, as manifested by a reduction of the amount of mRNA transcribed from the HAMP gene which may be isolated from a first cell or group of cells in which the HAMP gene is transcribed and which has or have been treated such that the expression of the HAMP gene is inhibited, as compared to a second cell or group of cells substantially identical to the first cell or group of cells but which has or have not been so treated (control cells). The degree of inhibition is usually expressed in terms of $$\frac{(\text{mRNA in control cells}) - (\text{mRNA in treated cells})}{(\text{mRNA in control cells})} \cdot 100\%$$

Alternatively, the degree of inhibition may be given in terms of a reduction of a parameter that is functionally linked to HAMP gene transcription, e.g. the amount of protein encoded by the HAMP gene which is secreted by a cell, or the number of cells displaying a certain phenotype, e.g apoptosis. In principle, HAMP gene silencing may be determined in any cell expressing the target, either constitutively or by genomic engineering, and by any appropriate assay. However, when a reference is needed in order to determine whether a given dsRNA inhibits the expression of the HAMP gene by a certain degree and therefore is encompassed by the instant invention, the assay provided in the Examples below shall serve as such reference.

For example, in certain instances, expression of the HAMP gene is suppressed by at least about 20%, 25%, 35%, or 50% by administration of the double-stranded oligonucleotide of the invention. In some embodiments, the HAMP gene is suppressed by at least about 60%, 70%, or 80% by administration of the double-stranded oligonucleotide of the invention. In some embodiments, the HAMP gene is suppressed by at least about 85%, 90%, or 95% by administration of the double-stranded oligonucleotide of the invention. Table 2 provides a wide range of values for inhibition of expression obtained in an in vitro assay using various HAMP dsRNA molecules at various concentrations.

As used herein in the context of HAMP expression, the terms "treat", "treatment", and the like, refer to relief from or alleviation of pathological processes which can be mediated by down regulating the HAMP gene. In the context of the present invention insofar as it relates to any of the other conditions recited herein below (other than pathological processes which can be mediated by down regulating the HAMP gene), the terms "treat", "treatment", and the like mean to relieve or alleviate at least one symptom associated with such condition, or to slow or reverse the progression of such condition. For example, in the context of anemia and other diseases associated with lowered iron levels, treatment will involve an increase in serum iron levels. Example patient populations that can benefit from such a treatment include, but are not limited to, individuals having anemia as a result of chronic renal failure, cancer patients, patients with chronic inflammatory disease as well as patients with chronic GI bleeding, such as with chronic ulcers or colon tumors.

As used herein, the phrases "therapeutically effective amount" and "prophylactically effective amount" refer to an amount that provides a therapeutic benefit in the treatment, prevention, or management of pathological processes which can be mediated by down regulating the HAMP gene on or an overt symptom of pathological processes which can be mediated by down regulating the HAMP gene. The specific amount that is therapeutically effective can be readily determined by ordinary medical practitioner, and may vary depending on factors known in the art, such as, e.g. the type of pathological processes which can be mediated by down regulating the HAMP gene, the patient's history and age, the stage of pathological processes which can be mediated by down regulating HAMP gene expression, and the administration of other anti-pathological processes which can be mediated by down regulating HAMP gene expression.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof and are described in more detail below. The term specifically excludes cell culture medium.

As used herein, a "transformed cell" is a cell into which a vector has been introduced from which a dsRNA molecule may be expressed.

II. Double-stranded Ribonucleic Acid (dsRNA)

In one embodiment, the invention provides double-stranded ribonucleic acid (dsRNA) molecules for inhibiting the expression of the HAMP gene in a cell or mammal, wherein the dsRNA comprises an antisense strand comprising a region of complementarity which is complementary to at least a part of an mRNA formed in the expression of the HAMP gene, and wherein the region of complementarity is less than 30 nucleotides in length, generally 19-24 nucleotides in length, and wherein said dsRNA, upon contact with a cell expressing said HAMP gene, inhibits the expression of said HAMP gene by at least 40%. The dsRNA comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of the HAMP gene, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc. In a preferred embodiment, the HAMP gene is the human HAMP gene. In specific embodiments, the antisense strand of the dsRNA comprises a strand selected from the sense sequences of Tables 1 or 3 and a second sequence selected from the group consisting of the antisense sequences of Tables 1 or 3. Alternative antisense agents that target elsewhere in the target sequence provided in Tables 1 or 3 can readily be determined using the target sequence and the flanking HAMP sequence.

In further embodiments, the dsRNA comprises at least one nucleotide sequence selected from the groups of sequences provided in Tables 1 or 3. In other embodiments, the dsRNA comprises at least two sequences selected from this group, wherein one of the at least two sequences is complementary to another of the at least two sequences, and one of the at least two sequences is substantially complementary to a sequence of an mRNA generated in the expression of the HAMP gene. Generally, the dsRNA comprises two oligonucleotides, wherein one oligonucleotide is described as the sense strand in Tables 1 or 3 and the second oligonucleotide is described as the antisense strand in Tables 1 or 3

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 1 or 3, the dsRNAs of the invention can comprise at least one strand of a length of minimally 21 nt. It can be reasonably expected that shorter dsRNAs comprising one of the sequences of Tables 1 or 3 minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of Tables 1 or 3, and differing in their ability to inhibit the expression of the HAMP gene in a FACS assay as described herein below by not more than 5, 10, 15, 20, 25, or 30% inhibition from a dsRNA comprising the full sequence, are contemplated by the invention. Further dsRNAs that cleave within the target sequence provided in Tables 1 or 3 can readily be made using the HAMP sequence and the target sequence provided.

In addition, the RNAi agents provided in Table 1 identify a site in the HAMP mRNA that is susceptible to RNAi based cleavage. As such the present invention further includes RNAi agents that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides from one of the sequences provided in Table 1 coupled to additional nucleotide sequences taken from the region contiguous to the selected sequence in the HAMP gene. For example, the last 15 nucleotides of SEQ ID NO:1 (minus the added AA sequences) combined with the next 6 nucleotides from the target HAMP gene produces a single strand agent of 21 nucleotides that is based on one of the sequences provided in Table 1.

The dsRNA of the invention can contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the HAMP gene, the dsRNA generally does not contain any mismatch within the central 13 nucleotides. The methods described within the invention can be used to determine whether a dsRNA containing a mismatch to a target sequence is effective in inhibiting the expression of the HAMP gene. Consideration of the efficacy of dsRNAs with mismatches in inhibiting expression of the HAMP gene is important, especially if the particular region of complementarity in the HAMP gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, modifications at other sites of the sugar or base of an oligonucleotide, introduction of non-natural bases into the oligonucleotide chain, covalent attachment to a ligand or chemical moiety, and replacement of internucleotide phosphate linkages with alternate linkages such as thiophosphates. More than one such modification may be employed.

Chemical linking of the two separate dsRNA strands may be achieved by any of a variety of well-known techniques, for example by introducing covalent, ionic or hydrogen bonds; hydrophobic interactions, van der Waals or stacking interactions; by means of metal-ion coordination, or through use of purine analogues. Generally, the chemical groups that can be used to modify the dsRNA include, without limitation, methylene blue; bifunctional groups, generally bis-(2-chloroethyl) amine; N-acetyl-N'-(p-glyoxylbenzoyl)cystamine; 4-thiouracil; and psoralen. In one embodiment, the linker is a hexaethylene glycol linker. In this case, the dsRNA are produced by solid phase synthesis and the hexa-ethylene glycol linker is incorporated according to standard methods (e.g., Williams, D. J., and K. B. Hall, *Biochem.* (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is generally formed by triple-helix bonds. Table 1 provides examples of modified RNAi agents of the invention.

In yet another embodiment, the nucleotides at one or both of the two single strands may be modified to prevent or inhibit the degradation activities of cellular enzymes, such as, for example, without limitation, certain nucleases. Techniques for inhibiting the degradation activity of cellular enzymes against nucleic acids are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, *Nat. Med.* (1995) 1:1116-8). Thus, at least one 2'-hydroxyl group of the nucleotides on a dsRNA is replaced by a chemical group, generally by a 2'-amino or a 2'-methyl group. Also, at least one nucleotide may be modified to form a locked nucleotide. Such locked nucleotide contains a methylene bridge that connects the 2'-oxygen of ribose with the 4'-carbon of ribose. Oligonucleotides containing the locked nucleotide are described in Koshkin, A. A., et al., *Tetrahedron* (1998), 54: 3607-3630) and Obika, S. et al., *Tetrahedron Lett.* (1998), 39: 5401-5404). Introduction of a locked nucleotide into an oligonucleotide improves the affinity for complementary sequences and increases the melting temperature by several degrees (Braasch, D. A. and D. R. Corey, *Chem. Biol.* (2001), 8:1-7).

Conjugating a ligand to a dsRNA can enhance its cellular absorption as well as targeting to a particular tissue or uptake by specific types of cells such as liver cells. In certain instances, a hydrophobic ligand is conjugated to the dsRNA to facilitate direct permeation of the cellular membrane and or uptake across the liver cells. Alternatively, the ligand conjugated to the dsRNA is a substrate for receptor-mediated endocytosis. These approaches have been used to facilitate cell permeation of antisense oligonucleotides as well as dsRNA agents. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. *Pharm. Res.* 1998, 15, 1540. Other ligands that have been conjugated to oligonucleotides include polyethylene glycols, carbohydrate clusters, cross-linking agents, porphyrin conjugates, delivery peptides and lipids such as cholesterol.

In certain instances, conjugation of a cationic ligand to oligonucleotides results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the invention via reaction of a selected serum-binding ligand with a linking moiety located on the 5' position of a nucleoside or oligonucleotide. In certain instances, an dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

In the ligand-conjugated dsRNA and ligand-molecule bearing sequence-specific linked nucleosides of the invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group. A summary listing of some of the oligonucleotide modifications known in the art is found at, for example, PCT Publication WO 200370918.

In some embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In one embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

Examples of modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Examples of modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate. The use of a cholesterol conjugate is particularly preferred since such a moiety can increase targeting liver cells cells, a site of HAMP expression.

Vector Encoded RNAi Agents

The dsRNA of the invention can also be expressed from recombinant viral vectors intracellularly in vivo. The recombinant viral vectors of the invention comprise sequences encoding the dsRNA of the invention and any suitable promoter for expressing the dsRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the dsRNA in a particular tissue or in a particular intracellular environment. The use of recombinant viral vectors to deliver dsRNA of the invention to cells in vivo is discussed in more detail below.

dsRNA of the invention can be expressed from a recombinant viral vector either as two separate, complementary RNA molecules, or as a single RNA molecule with two complementary regions.

Any viral vector capable of accepting the coding sequences for the dsRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Preferred viral vectors are those derived from AV and AAV. In a particularly preferred embodiment, the dsRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the dsRNA of the invention, a method for constructing the recombinant AV vector, and a method for delivering the vector into target cells, are described in Xia H et al. (2002), Nat. Biotech. 20: 1006-1010.

Suitable AAV vectors for expressing the dsRNA of the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

III. Pharmaceutical Compositions Comprising dsRNA

In one embodiment, the invention provides pharmaceutical compositions comprising a dsRNA, as described herein, and a pharmaceutically acceptable carrier. The pharmaceutical composition comprising the dsRNA is useful for treating a disease or disorder associated with the expression or activity of the HAMP gene, such as pathological processes which can be mediated by down regulating HAMP gene expression, such as anemia and other diseases associated with lowered iron levels. Such pharmaceutical compositions are formulated based on the mode of delivery. One example is compositions that are formulated for delivery to the liver via parenteral delivery.

The pharmaceutical compositions of the invention are administered in dosages sufficient to inhibit expression of the HAMP gene. The present inventors have found that, because of their improved efficiency, compositions comprising the dsRNA of the invention can be administered at surprisingly low dosages. A dosage of 5 mg dsRNA per kilogram body weight of recipient per day is sufficient to inhibit or suppress expression of the HAMP gene and may be administered systemically to the patient.

In general, a suitable dose of dsRNA will be in the range of 0.01 to 5.0 milligrams per kilogram body weight of the recipient per day, generally in the range of 1 microgram to 1 mg per kilogram body weight per day. The pharmaceutical composition may be administered once daily, or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes which can be mediated by down regulating HAMP gene expression. Such models are used for in vivo testing of dsRNA, as well as for determining a therapeutically effective dose.

Any method can be used to administer a dsRNA of the present invention to a mammal. For example, administration can be direct; oral; or parenteral (e.g., by subcutaneous, intraventricular, intramuscular, or intraperitoneal injection, or by intravenous drip). Administration can be rapid (e.g., by injection), or can occur over a period of time (e.g., by slow infusion or administration of slow release formulations).

Typically, when treating a mammal with anemia and other diseases associated with lowered iron levels, the dsRNA molecules are administered systemically via parental means. For example, dsRNAs, conjugated or unconjugate or formulated with or without liposomes, can be administered intravenously to a patient. For such, a dsRNA molecule can be formulated into compositions such as sterile and non-sterile aqueous solutions, non-aqueous solutions in common solvents such as alcohols, or solutions in liquid or solid oil bases. Such solutions also can contain buffers, diluents, and other suitable additives. For parenteral, intrathecal, or intraventricular administration, a dsRNA molecule can be formulated into compositions such as sterile aqueous solutions, which also can contain buffers, diluents, and other suitable additives (e.g., penetration enhancers, carrier compounds, and other pharmaceutically acceptable carriers).

In addition, dsRNA molecules can be administered to a mammal as biologic or abiologic means as described in, for example, U.S. Pat. No. 6,271,359. Abiologic delivery can be accomplished by a variety of methods including, without limitation, (1) loading liposomes with a dsRNA acid molecule provided herein and (2) complexing a dsRNA molecule with lipids or liposomes to form nucleic acid-lipid or nucleic acid-liposome complexes. The liposome can be composed of cationic and neutral lipids commonly used to transfect cells in vitro. Cationic lipids can complex (e.g., charge-associate) with negatively charged nucleic acids to form liposomes. Examples of cationic liposomes include, without limitation, lipofectin, lipofectamine, lipofectace, and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including Lipofectin.®. (Invitrogen/Life Technologies, Carlsbad, Calif.) and Effectene.™. (Qiagen, Valencia, Calif.). In addition, systemic delivery methods can be optimized using commercially available cationic lipids such as DDAB or DOTAP, each of which can be mixed with a neutral lipid such as DOPE or cholesterol. In some cases, liposomes such as those described by Templeton et al. (Nature Biotechnology, 15: 647-652 (1997)) can be used. In other embodiments, polycations such as polyethyleneimine can be used to achieve delivery in vivo and ex vivo (Boletta et al., J. Am Soc. Nephrol. 7: 1728 (1996)). Additional information regarding the use of liposomes to deliver nucleic acids can be found in U.S. Pat. No. 6,271,359, PCT Publication WO 96/40964 and Morrissey, D. et al. 2005. Nat Biotechnol. 23(8):1002-7.

Biologic delivery can be accomplished by a variety of methods including, without limitation, the use of viral vectors. For example, viral vectors (e.g., adenovirus and herpesvirus vectors) can be used to deliver dsRNA molecules to liver cells. Standard molecular biology techniques can be used to introduce one or more of the dsRNAs provided herein into one of the many different viral vectors previously developed to deliver nucleic acid to cells. These resulting viral vectors can be used to deliver the one or more dsRNAs to cells by, for example, infection.

dsRNAs of the present invention can be formulated in a pharmaceutically acceptable carrier or diluent. A "pharmaceutically acceptable carrier" (also referred to herein as an "excipient") is a pharmaceutically acceptable solvent, suspending agent, or any other pharmacologically inert vehicle. Pharmaceutically acceptable carriers can be liquid or solid, and can be selected with the planned manner of administration in mind so as to provide for the desired bulk, consistency, and other pertinent transport and chemical properties. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

In addition, dsRNA that target the HAMP gene can be formulated into compositions containing the dsRNA admixed, encapsulated, conjugated, or otherwise associated with other molecules, molecular structures, or mixtures of nucleic acids. For example, a composition containing one or more dsRNA agents that target the HAMP gene can contain other therapeutic agents such as other lipid lowering agents (e.g., statins).

Methods For Treating Diseases That Can Be Modulated By Down Regulating the Expression of HAMP The methods and compositions described herein can be used to treat diseases and conditions that can be modulated by down regulating HAMP gene expression. For example, the compositions described herein can be used to treat anemia and other diseases associated with lowered iron levels.

Methods For Inhibiting Expression of the HAMP Gene

In yet another aspect, the invention provides a method for inhibiting the expression of the HAMP gene in a mammal. The method comprises administering a composition of the invention to the mammal such that expression of the target HAMP gene is silenced. Because of their high specificity, the dsRNAs of the invention specifically target RNAs (primary or processed) of the target HAMP gene. Compositions and methods for inhibiting the expression of these HAMP genes using dsRNAs can be performed as described elsewhere herein.

In one embodiment, the method comprises administering a composition comprising a dsRNA, wherein the dsRNA comprises a nucleotide sequence which is complementary to at least a part of an RNA transcript of the HAMP gene of the mammal to be treated. When the organism to be treated is a mammal such as a human, the composition may be administered by any means known in the art including, but not limited to oral or parenteral routes, including intravenous, intramuscular, subcutaneous, transdermal, airway (aerosol) administration. In preferred embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Gene Walking of the HAMP Gene
Design And In Silico Selection of siRNAs Targeting Human Hepcidin siRNAs targeting either human or mouse hepcidin antimicrobial peptide (also referred to as hepcidin, official symbol: hamp, Genbank accession NM_021175.2 (human) and NM_032541.1 (mouse) were selected according to following criteria:
  a) predicted highest specificity in human or mouse
  or
  b) cross-reactivity to cynomolgous monkey (*macaca fascicularis*), rhesus monkey (*macaca mulatta*) and chimpanzee (*pan troglodytes*) and predicted highest specificity of siRNA antisense strand in human siRNAs with stretches of >=4 Gs in a row were excluded from the selection.

Specificity was predicted by fastA homology search algorithm and proprietary scripts and was defined as given, if every mRNA in the human RefSeq database (release 17, dowloaded on May, 9, 2006) except for hepcidin had either
  a) at least 2 mismatches to the siRNA sense and antisense sequence positions 10 to 18 (non-seed regions), with at least 1 mismatch in position 10 or 11 (cleavage site region) of the respective strand if only 2 mismatches were present, or
  b) at least 1 mismatch to the siRNA sense and antisense sequence positions 2 to 9 (seed region)

Primate sequences were assembled from genomic sequences (available on Jun. 8, 2006 at QFBase, Baylor College of Medicine and NCBI) previous to the selection in order to obtain information on conserved regions with human hepcidin, which were defined as candidate target regions for the set of cross-reactive siRNAs.

Table 1 provides an identification of siRNAs designed to selectively target the human hepcidin gene (with cross reactivity to orthologous hepcidin genes as described above).

Table 2 provides an identification of siRNAs designed to target the mouse hepcidin gene.

dsRNA synthesis
Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20 ° C. until use.

dsRNA Expression Vectors

In another aspect of the invention, HAMP specific dsRNA molecules that modulate HAMP gene expression activity are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., Proc. Natl. Acad. Sci. USA (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., *Curr. Topics Micro. Immunol*. (1992) 158:97-129)); adenovirus (see, for example, Berkner, et al., BioTechniques (1998) 6:616), Rosenfeld et al. (1991, *Science* 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or Ul snRNA promoter) or generally RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single HAMP gene or multiple HAMP genes over a period of a week or more are also contemplated by the invention. Successful introduction of the vectors of the invention into host cells can be monitored using various known methods. For example, transient transfection. can be signaled with a reporter, such as a fluorescent marker, such as Green Fluorescent Protein (GFP). Stable transfection. of ex vivo cells can be ensured using markers that provide the transfected cell with resistance to specific environmental factors (e.g., antibiotics and drugs), such as hygromycin B resistance.

The HAMP specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Those skilled in the art are familiar with methods and compositions in addition to those specifically set out in the instant disclosure which will allow them to practice this invention to the full scope of the claims hereinafter appended.

HAMP siRNA Screening COS-7 Cells

Cloning:

The cDNA sequences for human hepcidin and murine hepcidin-1 cDNA were synthesized thereby introducing a 5'-XhoI- and a 3'-NotI site and subcloned into pGA4 (Geneart AG, Regensburg, Germany). Human and mouse hepcidin were subcloned via the introduced XhoI- and NotI-sites into the multiple cloning site of the psiCheck-2 vector (Promega, Mannheim, Germany), which is located downstream of the Renilla translational stop codon. Correct subcloning was assured by sequencing (GATC Biotech, Konstanz, Germany).

Transfections:

Directly before plasmid transfection, Cos-7 cells (DSMZ, Braunschweig, Germany) were seeded at $1.5 \times 10^4$ cells/well on 96-well plates (Greiner Bio-One GmbH, Frickenhausen, Germany) in 75 µl of growth medium (Dulbecco's MEM, 10% fetal calf serum, 2 mM L-glutamine, 1.2 µg/ml sodium bicarbonate, 100 u penicillin/100 µg/ml streptomycin, all from Biochrom AG, Berlin, Germany). 50 ng of plasmid/well were transfected with Lipofectamine2000 (Invitrogen) as described below for the siRNAs, with the plasmid diluted in Opti-MEM to a final volume of 12.5 µl/well, prepared as a mastermix for the whole plate.

4h after the transfection of the plasmid, siRNA transfections were performed in quadruplicates. For each well 0.5 µl Lipofectamine2000 (Invitrogen GmbH, Karlsruhe, Germany) were mixed with 12 µl Opti-MEM (Invitrogen) and incubated for 15 min at room temperature. For the siRNA concentration being 50 nM in the 100 µl transfection volume, 1 µl of a 5 µM siRNA were mixed with 10.5 µl Opti-MEM per well, combined with the Lipofectamine2000-Opti-MEM mixture and again incubated for 15 minutes at room temperature. During that incubation time, growth medium was removed from cells and replaced by 75 µl/well of fresh medium. siRNA-Lipofectamine2000-complexes were applied completely (25 µl each per well) to the cells and cells were incubated for 24 h at 37° C. and 5% $CO_2$ in a humidified incubator (Heraeus GmbH, Hanau, Germany).

Cells were harvested by lysis with the appropriate buffer from the Dual-Glo Luciferase assay (Promega GmbH, Mannheim, Germany) and the assay was performed according to the kit's protocol. Values obtained from the Renilla-luciferase measurement were normalized with the respective values acquired in the Firefly-luciferase measurement as a transfection and loading control. Values acquired with siRNAs directed against the Renilla-luciferase-hepcidin fusion mRNA were normalized to the value obtained with an unspecific siRNA (directed against the neomycin resistance gene) which was set to 100%.

Effective siRNAs from the screen were further characterized by dose response curves. Transfections of dose response curves were performed in 6-fold dilutions starting with 100 nM down to 10 fM. Mock (no siRNA) was set to 100% expression level. siRNAs were diluted with Opti-MEM to a final volume of 12.5 µl according to the above protocol. (FIGS. 3 and 4, Table 1)

Figure 3:
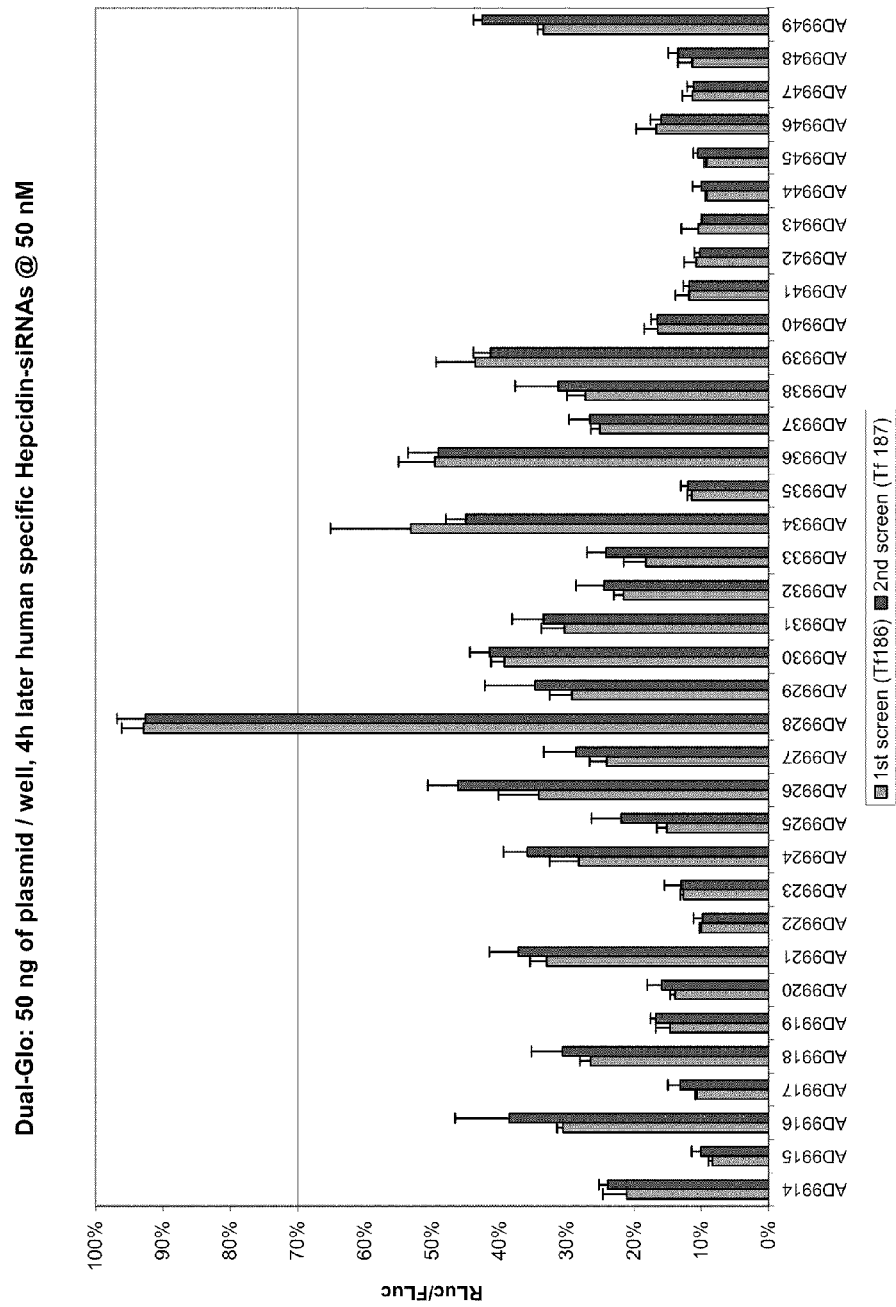
FIG. 3 is a graph showing the silencing activity of human hepcidin-siRNAs.
Figure 4:
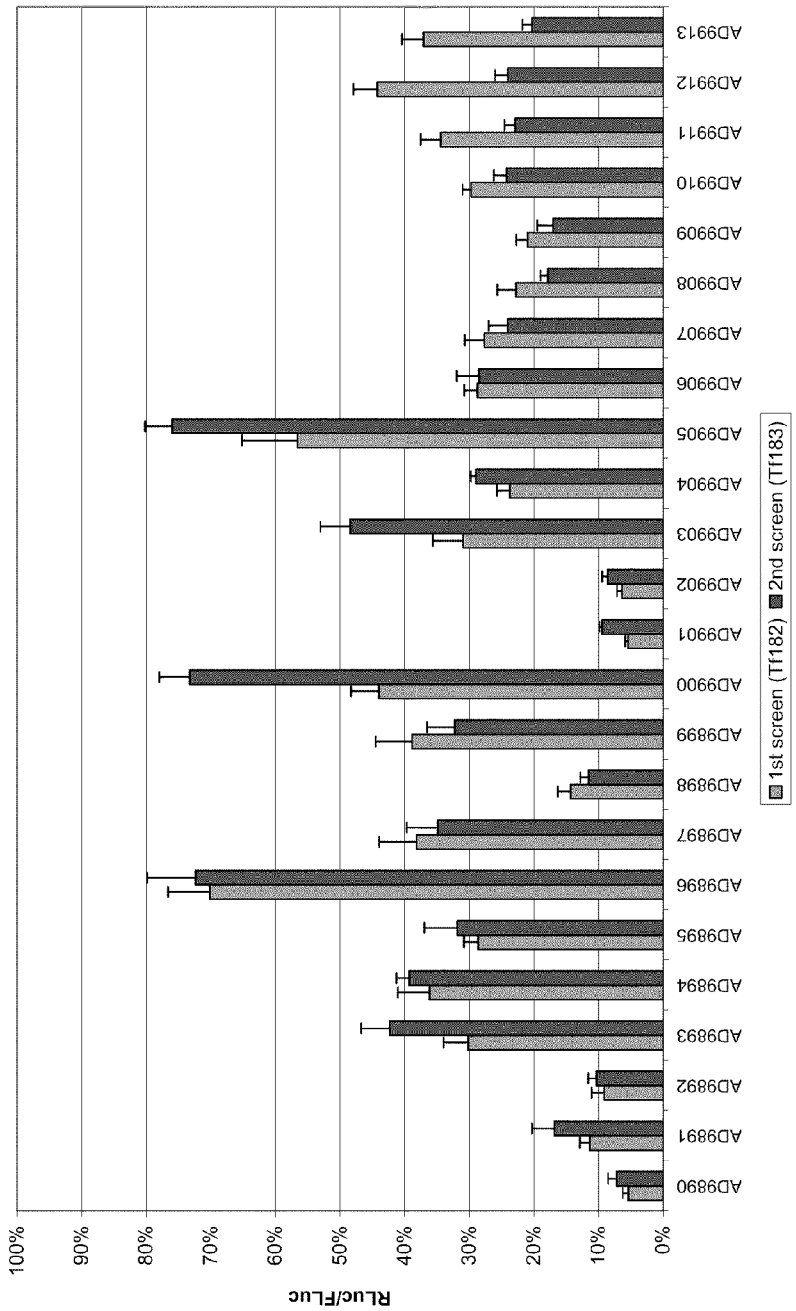
FIG. 4 is a graph showing the silencing activity of human hepcidin-siRNAs.

As can be seen in FIGS. 3 and 4 (summarized in Table 1), many active dsRNAs to hepcidin are identified.

The above screening procedure was repeated using the murine hepcidin gene as the target and the siRNAs of Table 2.

Stabilizing Modifications And Activity

Active duplexes identified above were then remade using modified bases and linkages in order to improve stability of the duplex and protect it from exo and endoribonuclease degradation. Table 3 (and Table 2 for murine selective siR-NAs) provides a listing of the duplexes made and the activities of these duplexes in the COS-7 assay described above. In Tables 2 and 3, a lower case "s" represents a phosphorothioate linkage and a lower case base, e.g. "u", represents a 2'OMe modified base, e.g. 2'OMe-U.

Figure 5:
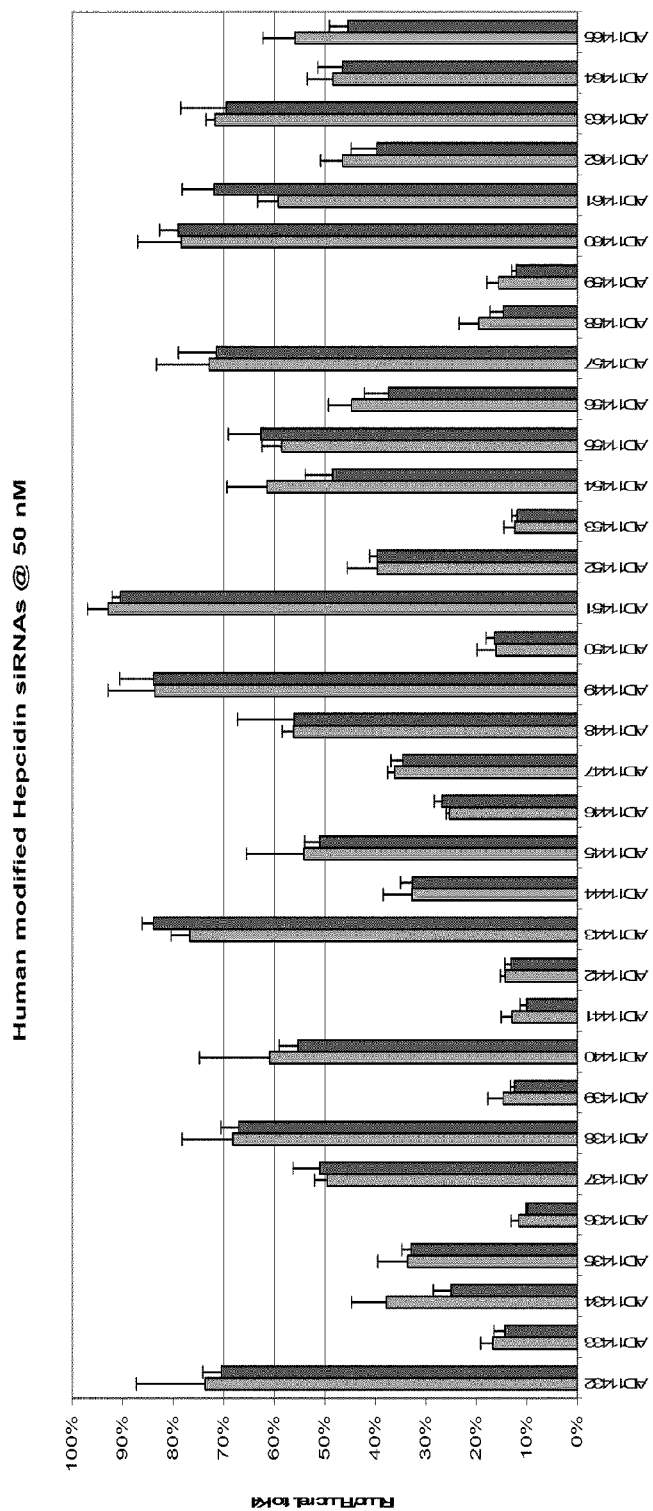
FIG. 5 is a graph showing the silencing activity of human hepcidin-siRNAs.
Figure 6:
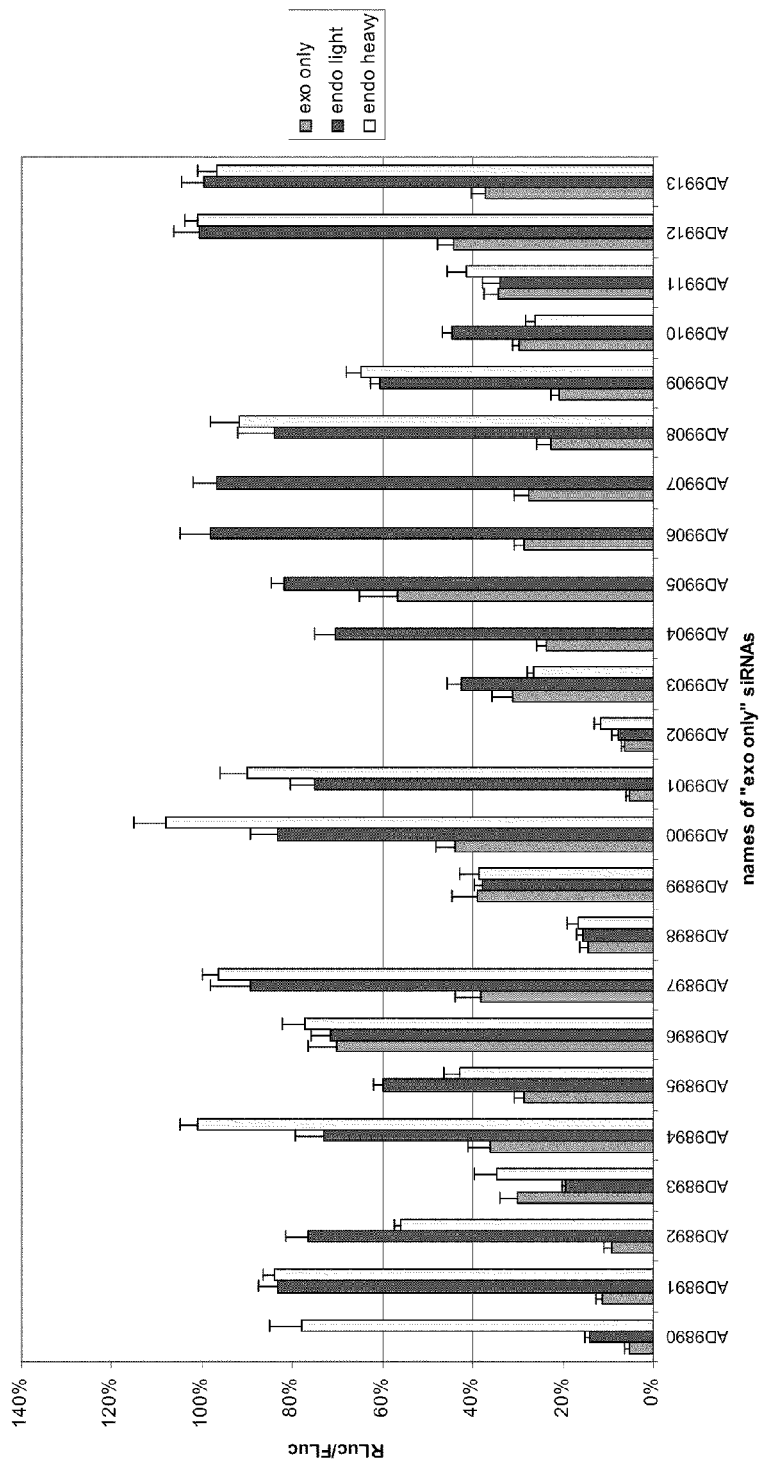
FIG. 6 is a graph showing the activity of mouse hepcidin siRNAs.

Activity is provided from a 50 nM screen (duplicates) for human siRNA in Table 3 (Table 2 for murine) and shown in FIG. 5 (FIG. 6 for murine). Further, IC50 values were determined as described above for several of the most active agents. The results are provided in Table 3.

Activity of Murine Hepcidin siRNA In Vivo

Experimental Methods

The efficacy of AD-10812 was determined in normal 10 week old 129s6/svEvTac mice using AD-1955 targeting luciferase as a control. These siRNAs were formulated in liposome (LNP-1) as described below and administered through i.v. bolus at a dose of 10 mg/kg (n=8). Forty eight hours after injection, the liver and serum samples were harvested. The liver Hamp1 and Hamp2 mRNA levels were determined by qRT-PCR using Hamp1 and Hamp2 specific primers and serum iron levels were determined using Feroxcine (Randox Life Sciences) and Hitachi 717 instrument.

Formulation of siRNAs In Liposomal Particles

Figure 7:
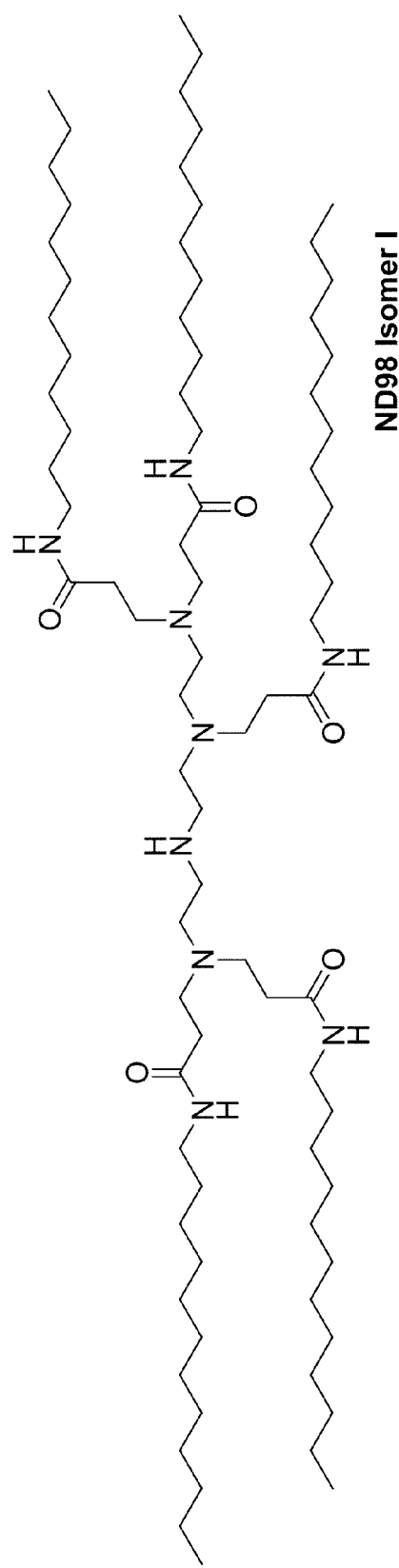
FIG. 7 shows the structure of the ND-98 lipid used in generating liposomes used for in vivo studies.

The lipidoid LNP-01, 4HCl (MW 1487) (FIG. 7), Cholesterol (Sigma-Aldrich), and PEG-Ceramide C16 (Avanti Polar Lipids) were used to prepare lipid-siRNA nanoparticles. Stock solutions of each in ethanol were prepared: LNP-01, 133 mg/mL; Cholesterol, 25 mg/mL, PEG-Ceramide C16, 100 mg/mL. LNP-01, Cholesterol, and PEG-Ceramide C16 stock solutions were then combined in a 42:48:10 molar ratio. Combined lipid solution was mixed rapidly with aqueous siRNA (in sodium acetate pH 5) such that the final ethanol concentration was 35-45% and the final sodium acetate concentration was 100-300 mM. Lipid-siRNA nanoparticles formed spontaneously upon mixing. Depending on the desired particle size distribution, the resultant nanoparticle mixture was in some cases extruded through a polycarbonate membrane (100 nm cut-off) using a thermobarrel extruder (Lipex Extruder, Northern Lipids, Inc). In other cases, the extrusion step was omitted. Ethanol removal and simultaneous buffer exchange was accomplished by either dialysis or tangential flow filtration. Buffer was exchanged to phosphate buffered saline (PBS) pH 7.2.

Characterization of Formulations

Formulations prepared by either the standard or extrusion-free method are characterized in a similar manner. Formulations are first characterized by visual inspection. They should be whitish translucent solutions free from aggregates or sediment. Particle size and particle size distribution of lipid-nanoparticles are measured by dynamic light scattering using a Malvern Zetasizer Nano ZS (Malvern, USA). Particles should be 20-300 nm, and ideally, 40-100 nm in size. The particle size distribution should be unimodal. The total siRNA concentration in the formulation, as well as the entrapped fraction, is estimated using a dye exclusion assay. A sample of the formulated siRNA is incubated with the RNA-binding dye Ribogreen (Molecular Probes) in the presence or absence of a formulation disrupting surfactant, 0.5% Triton-X100. The total siRNA in the formulation is determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%.

Results

Figure 8A:
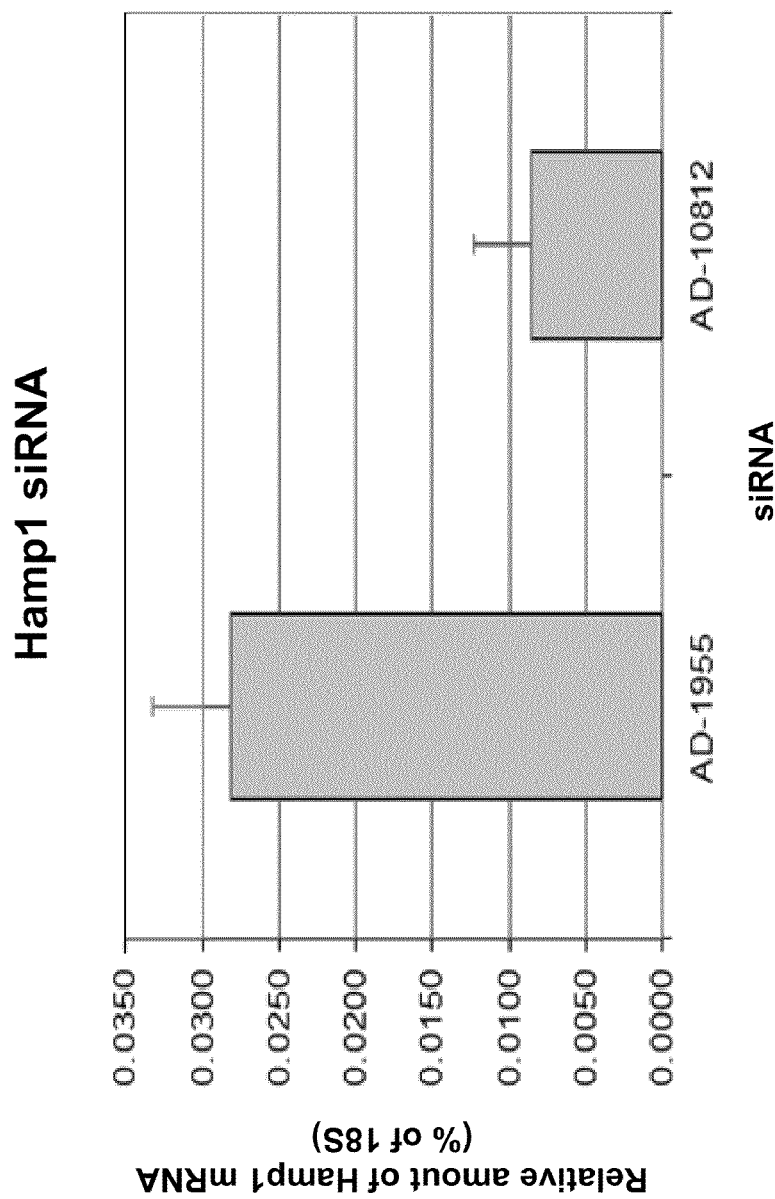
FIGS. 8A and 8B are graphs of in vivo activity of a liposomal formulated mouse hepcidin siRNA.
Figure 8B:
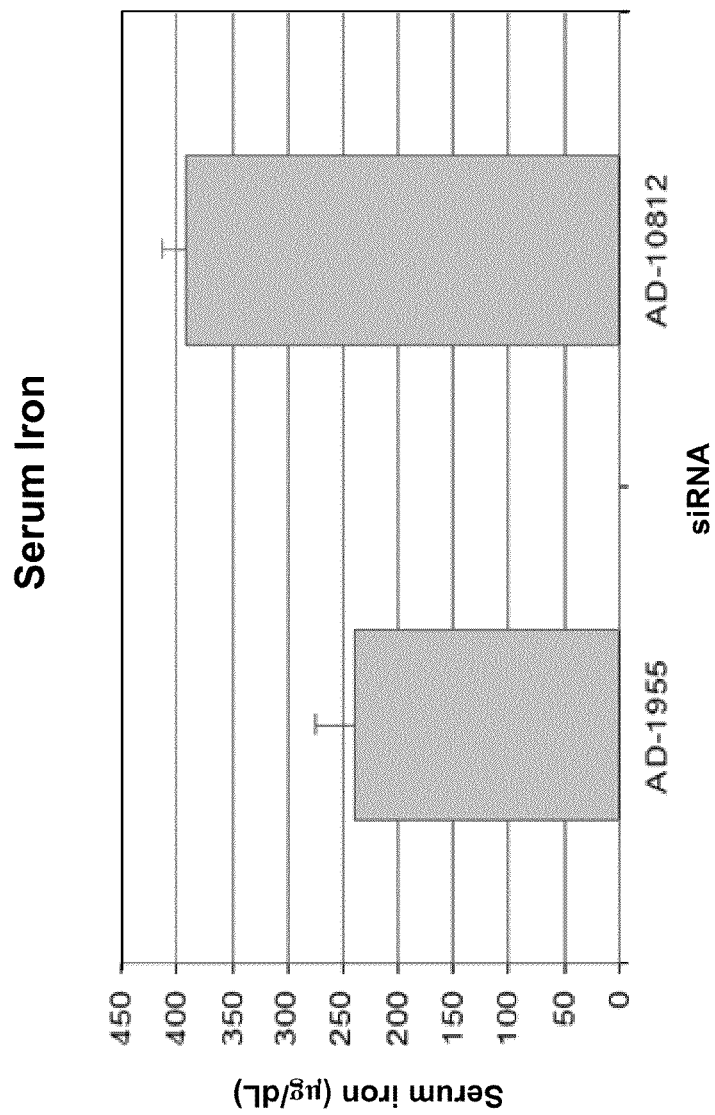

Approximately 70% reduction in Hamp1 mRNA levels and 64% increase in serum iron levels were achieved 48 h after administration of AD-10812 (FIG. 8: FIGS. 8A and 8B). AD-10812 did not reduce Hamp2 mRNA levels.

TABLE 1 hepcidin siRNAs, double overhang design, sense strand: dTsdT; antisense strand: dTsdT

| duplex name | position in human access. # | Sense sequence (5'-3') | SEQ ID NO | Antisense sequence (5'-3') | SEQ ID NO | % inhb (50 nM) | IC50 (nM) |
|---|---|---|---|---|---|---|---|
| AD-9914 | 378-396 | CCCAGAACAUAGGUCUUGGTsT | 1 | CCAAGACCUAUGUUCUGGGTsT | 37 | 78 | |
| AD-9915 | 283-301 | GCUGCUGUCAUCGAUCAAATsT | 2 | UUUGAUCGAUGACAGCAGCTsT | 38 | 91 | 0.091 |
| AD-9916 | 154-172 | CACAACAGACGGGACAACUTsT | 3 | AGUUGUCCCGUCUGUUGUGTsT | 39 | 65 | |
| AD-9917 | 56-74 | CCAGACAGACGGCACGAUGTsT | 4 | CAUCGUGCCGUCUGUCUGGTsT | 40 | 88 | 0.28 |
| AD-9918 | 312-330 | UGCUGCAAGACGUAGAACCTsT | 5 | GGUUCUACGUCUUGCAGCATsT | 41 | 72 | |
| AD-9919 | 238-256 | GAAGGAGGCGAGACACCCATsT | 6 | UGGGUGUCUCGCCUCCUUCTsT | 42 | 84 | 0.2 |
| AD-9920 | 315-333 | UGCAAGACGUAGAACCUACTsT | 7 | GUAGGUUCUACGUCUUGCATsT | 43 | 85 | 0.025 |
| AD-9921 | 158-176 | ACAGACGGGACAACUUGCATsT | 8 | UGCAAGUUGUCCCGUCUGUTsT | 44 | 65 | |
| AD-9922 | 291-309 | CAUCGAUCAAAGUGUGGGATsT | 9 | UCCCACACUUUGAUCGAUGTsT | 45 | 90 | 0.019 |
| AD-9923 | 57-75 | CAGACAGACGGCACGAUGGTsT | 10 | CCAUCGUGCCGUCUGUCUGTsT | 46 | 87 | 0.12 |

TABLE 1-continued hepcidin siRNAs, double overhang design, sense strand: dTsdT; antisense strand: dTsdT

| duplex name | position in human access. # | Sense sequence (5'-3') | SEQ ID NO | Antisense sequence (5'-3') | SEQ ID NO | % inhb (50 nM) | IC50 (nM) |
|---|---|---|---|---|---|---|---|
| AD-9924 | 236-254 | GCGAAGGAGGCGAGACACCTsT | 11 | GGUGUCUCGCCUCCUUCGCTsT | 47 | 68 | |
| AD-9925 | 243-261 | AGGCGAGACACCCACUUCCTsT | 12 | GGAAGUGGGUGUCUCGCCUTsT | 48 | 82 | 0.18 |
| AD-9926 | 4-22 | UGUCACUCGGUCCCAGACAUTsT | 13 | UGUCUGGGACCGAGUGACATsT | 49 | 60 | |
| AD-9927 | 317-335 | CAAGACGUAGAACCUACCUTsT | 14 | AGGUAGGUUCUACGUCUUGTsT | 50 | 74 | |
| AD-9928 | 6-24 | UCACUCGGUCCCAGACACCTsT | 15 | GGUGUCUGGGACCGAGUGATsT | 51 | 7 | |
| AD-9929 | 153-171 | CCACAACAGACGGGACAACTsT | 16 | GUUGUCCCGUCUGUUGUGGTsT | 52 | 68 | |
| AD-9930 | 156-174 | CAACAGACGGGACAACUUGTsT | 17 | CAAGUUGUCCCGUCUGUUGTsT | 53 | 60 | |
| AD-9931 | 318-336 | AAGACGUAGAACCUACCUGTsT | 18 | CAGGUAGGUUCUACGUCUUTsT | 54 | 69 | |
| AD-9932 | 225-243 | AUGUUCCAGAGGCGAAGGATsT | 19 | UCCUUCGCCUCUGGAACAUTsT | 55 | 77 | |
| AD-9933 | 223-241 | CCAUGUUCCAGAGGCGAAGTsT | 20 | CUUCGCCUCUGGAACAUGGTsT | 56 | 79 | |
| AD-9934 | 224-242 | CAUGUUCCAGAGGCGAAGGTsT | 21 | CCUUCGCCUCUGGAACAUGTsT | 57 | 51 | |
| AD-9935 | 314-332 | CUGCAAGACGUAGAACCUATsT | 22 | UAGGUUCUACGUCUUGCAGTsT | 58 | 89 | 0.11 |
| AD-9936 | 321-339 | ACGUAGAACCUACCUGCCCTsT | 23 | GGGCAGGUAGGUUCUACGUTsT | 59 | 51 | |
| AD-9937 | 288-306 | UGUCAUCGAUCAAAGUGUGTsT | 24 | CACACUUUGAUCGAUGACATsT | 60 | 74 | |
| AD-9938 | 58-76 | AGACAGACGGCACGAUGGCTsT | 25 | GCCAUCGUGCCGUCUGUCUTsT | 61 | 71 | |
| AD-9939 | 133-151 | UGACCAGUGGCUCUGUUUUTsT | 26 | AAAACAGAGCCACUGGUCATsT | 62 | 58 | |
| AD-9940 | 65-83 | CGGCACGAUGGCACUGAGCTsT | 27 | GCUCAGUGCCAUCGUGCCGTsT | 63 | 84 | 0.13 |
| AD-9941 | 285-303 | UGCUGUCAUCGAUCAAAGUTsT | 28 | ACUUUGAUCGAUGACAGCATsT | 64 | 88 | 0.061 |
| AD-9942 | 382-400 | GAACAUAGGUCUUGGAAUATsT | 29 | UAUUCCAAGACCUAUGUUCTsT | 65 | 90 | 0.016 |
| AD-9943 | 282-300 | GGCUGCUGUCAUCGAUCAATsT | 30 | UUGAUCGAUGACAGCAGCCTsT | 66 | 90 | 0.023 |
| AD-9944 | 284-302 | CUGCUGUCAUCGAUCAAAGTsT | 31 | CUUUGAUCGAUGACAGCAGTsT | 67 | 91 | 0.023 |
| AD-9945 | 280-298 | GCGGCUGCUGUCAUCGAUCTsT | 32 | GAUCGAUGACAGCAGCCGCTsT | 68 | 90 | 0.056 |
| AD-9946 | 286-304 | GCUGUCAUCGAUCAAAGUGTsT | 33 | CACUUUGAUCGAUGACAGCTsT | 69 | 84 | 0.11 |
| AD-9947 | 287-305 | CUGUCAUCGAUCAAAGUGUTsT | 34 | ACACUUUGAUCGAUGACAGTsT | 70 | 89 | 0.027 |
| AD-9948 | 289-307 | GUCAUCGAUCAAAGUGUGGTsT | 35 | CCACACUUUGAUCGAUGACTsT | 71 | 88 | 0.072 |
| AD-9949 | 155-173 | ACAACAGACGGGACAACUUTsT | 36 | AAGUUGUCCCGUCUGUUGUTsT | 72 | 62 | |

TABLE 2

Mouse cross reactive siRNAs: sequences and activity in COS-7 cells

Table 2A: Sequences

| position in mouse access. # | sense strand sequence (5'-3') | SEQ ID NO | antisense strand sequence (5'-3') | SEQ ID NO | duplex name |
|---|---|---|---|---|---|
| 171-189 | CAGACAUUGCGAUACCAAUTsT | 73 | AUUGGUAUCGCAAUGUCUGTsT | 145 | AD-9890 |
| 171-189 | cAGAcAuuGcGAuAccAAuTsT | 74 | AUUGGuAUCGcAAUGUCUGTsT | 146 | AD-10800 |
| 171-189 | cAGAcAuuGcGAuAccAAuTsT | 75 | AuuGGuAUCGcAAuGUCuGTsT | 147 | AD-10824 |

TABLE 2-continued

Mouse cross reactive siRNAs: sequences and activity in COS-7 cells

| Position | Sense | SEQ ID | Antisense | SEQ ID | AD # |
|---|---|---|---|---|---|
| 172-190 | AGACAUUGCGAUACCAAUGTsT | 76 | CAUUGGUAUCGCAAUGUCUTsT | 148 | AD-9891 |
| 172-190 | AGAcAuuGcGAuAccAAuGTsT | 77 | cAUUGGuAUCGcAAUGUCUTsT | 149 | AD-10801 |
| 172-190 | AGAcAuuGcGAuAccAAuGTsT | 78 | cAuuGGuAUCGcAAuGUCUTsT | 150 | AD-10825 |
| 170-188 | GCAGACAUUGCGAUACCAATsT | 79 | UUGGUAUCGCAAUGUCUGCTsT | 151 | AD-9892 |
| 170-188 | GcAGAcAuuGcGAuAccAATsT | 80 | UUGGuAUCGcAAUGUCUGCTsT | 152 | AD-10802 |
| 170-188 | GcAGAcAuuGcGAuAccAATsT | 81 | uuGGuAUCGcAAuGUCuGCTsT | 153 | AD-10826 |
| 284-302 | UAGCCUAGAGCCACAUCCUTsT | 82 | AGGAUGUGGCUCUAGGCUATsT | 154 | AD-9893 |
| 284-302 | uAGccuAGAGccAcAuccuTsT | 83 | AGGAUGUGGCUCuAGGCuATsT | 155 | AD-10803 |
| 284-302 | uAGccuAGAGccAcAuccuTsT | 84 | AGGAuGuGGCUCuAGGCuATsT | 156 | AD-10827 |
| 173-191 | GACAUUGCGAUACCAAUGCTsT | 85 | GCAUUGGUAUCGCAAUGUCTsT | 157 | AD-9894 |
| 173-191 | GAcAuuGcGAuAccAAuGcTsT | 86 | GcAUUGGuAUCGcAAUGUCTsT | 158 | AD-10804 |
| 173-191 | GAcAuuGcGAuAccAAuGcTsT | 87 | GcAuuGGuAUCGcAAuGUCTsT | 159 | AD-10828 |
| 177-195 | UUGCGAUACCAAUGCAGAATsT | 88 | UUCUGCAUUGGUAUCGCAATsT | 160 | AD-9895 |
| 177-195 | uuGcGAuAccAAuGcAGAATsT | 89 | UUCUGcAUUGGuAUCGcAATsT | 161 | AD-10805 |
| 177-195 | uuGcGAuAccAAuGcAGAATsT | 90 | uUCuGcAuuGGuAUCGcAATsT | 162 | AD-10829 |
| 178-196 | UGCGAUACCAAUGCAGAAGTsT | 91 | CUUCUGCAUUGGUAUCGCATsT | 163 | AD-9896 |
| 178-196 | uGcGAuAccAAuGcAGAAGTsT | 92 | CUUCUGcAUUGGuAUCGcATsT | 164 | AD-10806 |
| 178-196 | uGcGAuAccAAuGcAGAAGTsT | 93 | CuUCuGcAuuGGuAUCGcATsT | 165 | AD-10830 |
| 100-118 | CACCACCUAUCUCCAUCAATsT | 94 | UUGAUGGAGAUAGGUGGUGTsT | 166 | AD-9897 |
| 100-118 | cAccAccuAucuccAucAATsT | 95 | UUGAUGGAGAuAGGUGGUGTsT | 167 | AD-10807 |
| 100-118 | cAccAccuAucuccAucAATsT | 96 | uuGAuGGAGAuAGGuGGuGTsT | 168 | AD-10831 |
| 120-138 | AGAUGAGACAGACUACAGATsT | 97 | UCUGUAGUCUGUCUCAUCUTsT | 169 | AD-9898 |
| 120-138 | AGAuGAGAcAGAcuAcAGATsT | 98 | UCUGuAGUCUGUCuCAUCUTsT | 170 | AD-10808 |
| 120-138 | AGAuGAGAcAGAcuAcAGATsT | 99 | UCuGuAGUCuGUCuCAUCUTsT | 171 | AD-10832 |
| 176-194 | AUUGCGAUACCAAUGCAGATsT | 100 | UCUGCAUUGGUAUCGCAAUTsT | 172 | AD-9899 |
| 176-194 | AuuGcGAuAccAAuGcAGATsT | 101 | UCUGcAUUGGuAUCGcAAUTsT | 173 | AD-10809 |
| 176-194 | AuuGcGAuAccAAuGcAGATsT | 102 | UCuGcAuuGGuAUCGcAAUTsT | 174 | AD-10833 |
| 372-390 | AAUAAAGACGAUUUUAUUUTsT | 103 | AAAUAAAAUCGUCUUUAUUTsT | 175 | AD-9900 |
| 372-390 | AAuAAAGAcGAuuuuAuuuTsT | 104 | AAAuAAAAUCGUCUUuAUUTsT | 176 | AD-10810 |
| 372-390 | AAuAAAGAcGAuuuuAuuuTsT | 105 | AAAuAAAAUCGUCuuuAuUTsT | 177 | AD-10834 |
| 169-187 | GGCAGACAUUGCGAUACCATsT | 106 | UGGUAUCGCAAUGUCUGCCTsT | 178 | AD-9901 |
| 169-187 | GGcAGAcAuuGcGAuAccATsT | 107 | UGGuAUCGcAAUGUCUGCCTsT | 179 | AD-10811 |
| 169-187 | GGcAGAcAuuGcGAuAccATsT | 108 | uGGuAUCGcAAuGUCuGCCTsT | 180 | AD-10835 |
| 245-263 | UGCUGUAACAAUUCCCAGUTsT | 109 | ACUGGGAAUUGUUACAGCATsT | 181 | AD-9902 |
| 245-263 | uGcuGuAAcAAuucccAGuTsT | 110 | ACUGGGAAUUGUuAcAGcATsT | 182 | AD-10812 |
| 245-263 | uGcuGuAAcAAuucccAGuTsT | 111 | ACuGGGAAuuGuuAcAGcATsT | 183 | AD-10836 |
| 231-249 | UCUUCUGCUGUAAAUGCUGTsT | 112 | CAGCAUUUACAGCAGAAGATsT | 184 | AD-9903 |
| 231-249 | ucuucuGcuGuAAAuGcuGTsT | 113 | cAGcAUUuAcAGcAGAAGATsT | 185 | AD-10813 |
| 231-249 | ucuucuGcuGuAAAuGcuGTsT | 114 | cAGcAuuuAcAGcAGAAGATsT | 186 | AD-10837 |

TABLE 2-continued

Mouse cross reactive siRNAs: sequences and activity in COS-7 cells

| | | | | | |
|---|---|---|---|---|---|
| 60-78 | CUGCCUGUCUCCUGCUUCUTsT | 115 | AGAAGCAGGAGACAGGCAGTsT | 187 | AD-9904 |
| 60-78 | cuGccuGucuccuGcuucuTsT | 116 | AGAAGcAGGAGAcAGGCAGTsT | 188 | AD-10814 |
| 60-78 | cuGccuGucuccuGcuucuTsT | 117 | AGAAGcAGGAGAcAGGcAGTsT | 189 | |
| 61-79 | UGCCUGUCUCCUGCUUCUCTsT | 118 | GAGAAGCAGGAGACAGGCATsT | 190 | AD-9905 |
| 61-79 | uGccuGucuccuGcuucucTsT | 119 | GAGAAGcAGGAGAcAGGcATsT | 191 | AD-10815 |
| 61-79 | uGccuGucuccuGcuucucTsT | 120 | GAGAAGcAGGAGAcAGGcATsT | 192 | |
| 59-77 | GCUGCCUGUCUCCUGCUUCTsT | 121 | GAAGCAGGAGACAGGCAGCTsT | 193 | AD-9906 |
| 59-77 | GcuGccuGucuccuGcuucTsT | 122 | GAAGcAGGAGAcAGGcAGCTsT | 194 | AD-10816 |
| 59-77 | GcuGccuGucuccuGcuucTsT | 123 | GAAGcAGGAGAcAGGcAGCTsT | 195 | |
| 62-80 | GCCUGUCUCCUGCUUCUCCTsT | 124 | GGAGAAGCAGGAGACAGGCTsT | 196 | AD-9907 |
| 62-80 | GccuGucuccuGcuucuccTsT | 125 | GGAGAAGcAGGAGAcAGGCTsT | 197 | AD-10817 |
| 62-80 | GccuGucuccuGcuucuccTsT | 126 | GGAGAAGcAGGAGAcAGGCTsT | 198 | |
| 56-74 | CAGGCUGCCUGUCUCCUGCTsT | 127 | GCAGGAGACAGGCAGCCUGTsT | 199 | AD-9908 |
| 56-74 | cAGGcuGccuGucuccuGcTsT | 128 | GcAGGAGAcAGGcAGCCUGTsT | 200 | AD-10818 |
| 56-74 | cAGGcuGccuGucuccuGcTsT | 129 | GcAGGAGAcAGGcAGCCuGTsT | 201 | AD-10838 |
| 232-250 | CUUCUGCUGUAAAUGCUGUTsT | 130 | ACAGCAUUUACAGCAGAAGTsT | 202 | AD-9909 |
| 232-250 | cuucuGcuGuAAAuGcuGuTsT | 131 | AcAGcAUUuAcAGcAGAAGTsT | 203 | AD-10819 |
| 232-250 | cuucuGcuGuAAAuGcuGuTsT | 132 | AcAGcAuuuAcAGcAGAAGTsT | 204 | AD-10839 |
| 233-251 | UUCUGCUGUAAAUGCUGUATsT | 133 | UACAGCAUUUACAGCAGAATsT | 205 | AD-9910 |
| 233-251 | uucuGcuGuAAAuGcuGuATsT | 134 | uAcAGcAUUuAcAGcAGAATsT | 206 | AD-10820 |
| 233-251 | uucuGcuGuAAAuGcuGuATsT | 135 | uAcAGcAuuuAcAGcAGAATsT | 207 | AD-10840 |
| 234-252 | UCUGCUGUAAAUGCUGUAATsT | 136 | UUACAGCAUUUACAGCAGATsT | 208 | AD-9911 |
| 234-252 | ucuGcuGuAAAuGcuGuAATsT | 137 | UuAcAGcAUUuAcAGcAGATsT | 209 | AD-10821 |
| 234-252 | ucuGcuGuAAAuGcuGuAATsT | 138 | uuAcAGcAuuuAcAGcAGATsT | 210 | AD-10841 |
| 57-75 | AGGCUGCCUGUCUCCUGCUTsT | 139 | AGCAGGAGACAGGCAGCCUTsT | 211 | AD-9912 |
| 57-75 | AGGcuGccuGucuccuGcuTsT | 140 | AGcAGGAGAcAGGcAGCCUTsT | 212 | AD-10822 |
| 57-75 | AGGcuGccuGucuccuGcuTsT | 141 | AGcAGGAGAcAGGcAGccUTsT | 213 | AD-10842 |
| 58-76 | GGCUGCCUGUCUCCUGCUUTsT | 142 | AAGCAGGAGACAGGCAGCCTsT | 214 | AD-9913 |
| 58-76 | GGcuGccuGucuccuGcuuTsT | 143 | AAGcAGGAGAcAGGcAGCCTsT | 215 | AD-10823 |
| 58-76 | GGcuGccuGucuccuGcuuTsT | 144 | AAGcAGGAGAcAGGcAGccTsT | 216 | AD-10843 |

Table 2B. Activity.

| position in mouse access. # | duplex name | % inhib at 50 nM (%) | IC50 (uM) |
|---|---|---|---|
| 171-189 | AD-9890 | 95 | 0.052 |
| 171-189 | AD-10800 | 86 | 0.056 |
| 171-189 | AD-10824 | 22 | |
| 172-190 | AD-9891 | 89 | 0.15 |
| 172-190 | AD-10801 | 17 | |
| 172-190 | AD-10825 | 16 | |

TABLE 2-continued

Mouse cross reactive siRNAs: sequences and activity in COS-7 cells

| | | | |
|---|---|---|---|
| 170-188 | AD-9892 | 91 | 0.099 |
| 170-188 | AD-10802 | 23 | |
| 170-188 | AD-10826 | 44 | |
| 284-302 | AD-9893 | 70 | |
| 284-302 | AD-10803 | 80 | 0.34 |
| 284-302 | AD-10827 | 65 | |
| 173-191 | AD-9894 | 64 | |
| 173-191 | AD-10804 | 27 | |
| 173-191 | AD-10828 | 0 | |
| 177-195 | AD-9895 | 71 | |
| 177-195 | AD-10805 | 40 | |
| 177-195 | AD-10829 | 57 | |
| 178-196 | AD-9896 | 30 | |
| 178-196 | AD-10806 | 26 | |
| 178-196 | AD-10830 | 23 | |
| 100-118 | AD-9897 | 62 | |
| 100-118 | AD-10807 | 11 | |
| 100-118 | AD-10831 | 3 | |
| 120-138 | AD-9898 | 86 | 0.031 |
| 120-138 | AD-10808 | 85 | 0.076 |
| 120-138 | AD-10832 | 83 | 14 |
| 176-194 | AD-9899 | 61 | |
| 176-194 | AD-10809 | 62 | |
| 176-194 | AD-10833 | 61 | |
| 372-390 | AD-9900 | 56 | |
| 372-390 | AD-10810 | 17 | |
| 372-390 | AD-10834 | 0 | |
| 169-187 | AD-9901 | 95 | 0.096 |
| 169-187 | AD-10811 | 25 | |
| 169-187 | AD-10835 | 10 | |
| 245-263 | AD-9902 | 94 | 0.032 |
| 245-263 | AD-10812 | 92 | 0.03 |
| 245-263 | AD-10836 | 88 | 0.065 |
| 231-249 | AD-9903 | 69 | |
| 231-249 | AD-10813 | 58 | |
| 231-249 | AD-10837 | 73 | 11 |
| 60-78 | AD-9904 | 76 | |
| 60-78 | AD-10814 | 29 | |
| 60-78 | | | |

TABLE 2-continued

Mouse cross reactive siRNAs: sequences and activity in COS-7 cells

| | | | |
|---|---|---|---|
| 61-79 | AD-9905 | 43 | |
| 61-79 | AD-10815 | 18 | |
| 61-79 | | | |
| 59-77 | AD-9906 | 71 | |
| 59-77 | AD-10816 | 2 | |
| 59-77 | | | |
| 62-80 | AD-9907 | 72 | |
| 62-80 | AD-10817 | 3 | |
| 62-80 | | | |
| 56-74 | AD-9908 | 76 | |
| 56-74 | AD-10818 | 16 | |
| 56-74 | AD-10838 | 8 | |
| 232-250 | AD-9909 | 79 | |
| 232-250 | AD-10819 | 39 | |
| 232-250 | AD-10839 | 35 | |
| 233-251 | AD-9910 | 70 | |
| 233-251 | AD-10820 | 55 | |
| 233-251 | AD-10840 | 74 | 2.7 |
| 234-252 | AD-9911 | 66 | |
| 234-252 | AD-10821 | 66 | |
| 234-252 | AD-10841 | 58 | |
| 57-75 | AD-9912 | 56 | |
| 57-75 | AD-10822 | 0 | |
| 57-75 | AD-10842 | 0 | |
| 58-76 | AD-9913 | 63 | |
| 58-76 | AD-10823 | 0 | |
| 58-76 | AD-10843 | 3 | |

TABLE 3

Modified duplexes: sequences and activity in COS-7 cells

Table 3A: Sequences

| position in human access. # | parent Duplex | Sense strand sequence (5'-3') | SEQ ID NO | Antisense strand sequence (5'-3') | SEQ ID NO | duplex name |
|---|---|---|---|---|---|---|
| 283-301 | AD-9915 | GcuGcuGucAucGAucAAATsT | 217 | uuuGAUCGAuGAcAGcAGCTsT | 234 | AD-11449 |
| 56-74 | AD-9917 | ccAGAcAGAcGGcAcGAuGTsT | 218 | cAUCGuGCCGUCuGUCuGGTsT | 235 | AD-11450 |
| 238-256 | AD-9919 | GAAGGAGGcGAGAcAcccATsT | 219 | uGGGuGUCUCGCCUCCuUCTsT | 236 | AD-11451 |
| 315-333 | AD-9920 | uGcAAGAcGuAGAAccuAcTsT | 220 | GuAGGuUCuACGUCuUGcATsT | 237 | AD-11452 |
| 291-309 | AD-9922 | cAucGAucAAAGuGuGGGATsT | 221 | UCCcAcACuuuGAUCGAuGTsT | 238 | AD-11453 |

TABLE 3-continued

Modified duplexes: sequences and activity in COS-7 cells

| | | | | | |
|---|---|---|---|---|---|
| 57-75 | AD-9923 | cAGAcAGAcGGcAcGAuGGTsT | 222 | CcAUCGuGCCGUCuGUCuGTsT | 239 | AD-11454 |
| 243-261 | AD-9925 | AGGcGAGAcAcccAcuuccTsT | 223 | GGAAGuGGGuGUCUCGCCUTsT | 240 | AD-11455 |
| 314-332 | AD-9935 | cuGcAAGAcGuAGAAccuATsT | 224 | uAGGuUCuACGUCuuGcAGTsT | 241 | AD-11456 |
| 65-83 | AD-9940 | cGGcAcGAuGGcAcuGAGcTsT | 225 | GCUcAGuGCcAUCGuGCCGTsT | 242 | AD-11457 |
| 285-303 | AD-9941 | uGcuGucAucGAucAAAGuTsT | 226 | ACuuuGAUCGAuGAcAGcATsT | 243 | AD-11458 |
| 382-400 | AD-9942 | GAAcAuAGGucuuGGAAuATsT | 227 | uAuUCcAAGACCuAuGuUCTsT | 244 | AD-11459 |
| 282-300 | AD-9943 | GGcuGcuGucAucGAucAATsT | 228 | uuGAUCGAuGAcAGcAGCCTsT | 245 | AD-11460 |
| 284-302 | AD-9944 | cuGcuGucAucGAucAAAGTsT | 229 | CuuuGAUCGAuGAcAGcAGTsT | 246 | AD-11461 |
| 280-298 | AD-9945 | GcGGcuGcuGucAucGAucTsT | 230 | GAUCGAuGAcAGcAGCCGCTsT | 247 | AD-11462 |
| 286-304 | AD-9946 | GcuGucAucGAucAAAGuGTsT | 231 | cACuuuGAUCGAuGAcAGCTsT | 248 | AD-11463 |
| 287-305 | AD-9947 | cuGucAucGAucAAAGuGuTsT | 232 | AcACuuuGAUCGAuGAcAGTsT | 249 | AD-11464 |
| 289-307 | AD-9948 | GucAucGAucAAAGuGuGGTsT | 233 | CcAcACuuuGAUCGAuGACTsT | 250 | AD-11465 |

Table 3B: Activity

| position in human access. # | parent Duplex | duplex name | % inhib | IC50(nM) |
|---|---|---|---|---|
| 283-301 | AD-9915 | AD-11449 | 16 | |
| 56-74 | AD-9917 | AD-11450 | 84 | 4.04 |
| 238-256 | AD-9919 | AD-11451 | 10 | |
| 315-333 | AD-9920 | AD-11452 | 60 | |
| 291-309 | AD-9922 | AD-11453 | 88 | 0.33 |
| 57-75 | AD-9923 | AD-11454 | 52 | |
| 243-261 | AD-9925 | AD-11455 | 37 | |
| 314-332 | AD-9935 | AD-11456 | 63 | |
| 65-83 | AD-9940 | AD-11457 | 29 | |
| 285-303 | AD-9941 | AD-11458 | 85 | 0.66 |
| 382-400 | AD-9942 | AD-11459 | 88 | 0.18 |
| 282-300 | AD-9943 | AD-11460 | 21 | |
| 284-302 | AD-9944 | AD-11461 | 28 | |
| 280-298 | AD-9945 | AD-11462 | 60 | |
| 286-304 | AD-9946 | AD-11463 | 31 | |
| 287-305 | AD-9947 | AD-11464 | 53 | |
| 289-307 | AD-9948 | AD-11465 | 55 | |

We claim:

1. A method for inhibiting the expression of the hepicidin (HAMP) gene in a cell, comprising:
   introducing into the cell a double-stranded RNA (dsRNA), wherein the dsRNA comprises a sense strand consisting of the nucleotide sequence of SEQ ID NO:29 and an antisense strand consisting of the nucleotide sequence of SEQ ID NO:65; and
   maintaining the cell for a time sufficient to obtain degradation of the mRNA transcript of the HAMP gene, thereby inhibiting expression of the HAMP gene in the cell.

2. The method of claim 1, wherein the dsRNA comprises at least one modified nucleotide.

3. The method of claim 2, wherein the modified nucleotide is selected from the group consisting of: a 2'-O-methyl modified nucleotide, a nucleotide comprising a 5'-phosphorothioate group, and a terminal nucleotide linked to a cholesteryl derivative or dodecanoic acid bisdecylamide group.

4. The method of claim 2, wherein the modified nucleotide is selected from the group consisting of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

5. The method of claim 1, wherein the sense strand is modified as follows: GAAcAuAGGucuuGGAAuATsT (SEQ ID NO:227) and the antisense strand is modified as follows: uAuUCcAAGACCuAuGuUCTs (SEQ ID NO:244), wherein "c" indicates a 2'-O-methyl modified cytodine; "u" indicates a 2'-O-methyl modified uracil, and sT indicates a 5'-phosphorothioate modified thymidine.

6. The method of claim 1, wherein the sense strand consists of SEQ ID NO:227 and the antisense strand consists of SEQ ID NO:244.

7. A method of treating or managing pathological processes which can be mediated by down regulating HAMP gene expression, comprising:
   administering to a subject in need of such treatment or management a therapeutically effective amount of a dsRNA, wherein the dsRNA comprises a sense strand consisting of the nucleotide sequence of SEQ ID NO:29 and an antisense strand consisting of the nucleotide sequence of SEQ ID NO:65, and wherein administration of the dsRNA results in treating or managing the pathological processes which can be mediated by down regulating HAMP gene expression.

8. The method of claim 7, wherein the sense strand is modified as follows: GAAcAuAGGucuuGGAAuATsT (SEQ ID NO:227) and the antisense strand is modified as follows: uAuUCcAAGACCuAuGuUCTs (SEQ ID NO:244), wherein "c" indicates a 2'-O-methyl modified cytodine; "u" indicates a 2'-O-methyl modified uracil, and sT indicates a 5'-phosphorothioate modified thymidine.

9. The method of claim 7, wherein the sense strand consists of SEQ ID NO:227 and the antisense strand consists of SEQ ID NO:244.

10. The method of claim 7, wherein the pathological process is a disease associated with lowered iron levels.

11. The method of claim 7, wherein the pathological process is inflammation.

12. The method of claim 7, wherein the pathological process is anemia.

13. The method of claim 7, wherein the pathological process is anemia of chronic disease.

14. The method of claim 7, wherein the pathological process is haemochromatosis.

15. The method of claim 7, wherein the dsRNA is administered subcutaneously.

16. The method of claim 7, wherein the dsRNA is administered intravenously.

17. The method of claim 7, wherein the administration of dsRNA results in an increase in serum iron levels in the subject.

18. The method of claim 7, wherein the subject has chronic renal failure, cancer, chronic inflammatory disease, chronic gastrointestinal (GI) bleeding, a chronic ulcer, or a colon tumor.

19. The method of claim 1, wherein the cell is a liver cell.

20. The method of claim 7, wherein the pathological process is anemia of chronic disease, wherein the dsRNA is administered subcutaneously, and wherein administration of the dsRNA results in an increase in serum iron levels in the subject.

21. The method of claim 7, wherein the pathological process is anemia of chronic disease, wherein the dsRNA is administered intravenously, and wherein administration of the dsRNA results in an increase in serum iron levels in the subject.

22. The method of claim 1, wherein the cell is a COS-7 cell, wherein the dsRNA is at a concentration of 50 nM, and wherein expression of the HAMP gene is inhibited by 90% compared to a control.

23. The method of claim 1, wherein the cell is a COS-7 cell, wherein the dsRNA is at a concentration of 50 nM, and wherein expression of the HAMP gene is inhibited by 88% compared to a control.

24. The method of claim 7, wherein the dsRNA is formulated in a lipid formulation.

* * * * *

SEQUENCE LISTING

<160> NUMBER OF SEQ ID NOS: 250

<210> SEQ ID NO 1
<211> LENGTH: 21
<212> TYPE: DNA
<213> ORGANISM: Artificial sequence
<220> FEATURE:

```
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 1
cccagaacau aggucuuggt t                                             21

<210> SEQ ID NO 2
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 2
gcugcuguca ucgaucaaat t                                             21

<210> SEQ ID NO 3
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 3
cacaacagac gggacaacut t                                             21

<210> SEQ ID NO 4
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
```

-continued

<223> OTHER INFORMATION: /mod_base = "2'-hydroxy corresponding base"

<400> SEQUENCE: 4
ccagacagac ggcacgaugt t                                             21

<210> SEQ ID NO 5
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 5
ugcugcaaga cguagaacct t                                             21

<210> SEQ ID NO 6
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 6
gaaggaggcg agacacccat t                                             21

<210> SEQ ID NO 7
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 7
ugcaagacgu agaaccuact t                                             21

<210> SEQ ID NO 8
<211> LENGTH: 21
<212> TYPE: DNA
<213> ORGANISM: Artificial sequence

```
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 8
acagacggga caacuugcat t                                              21

<210> SEQ ID NO 9
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 9
caucgaucaa aguugggat t                                               21

<210> SEQ ID NO 10
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 10
cagacagacg gcacgauggt t                                              21

<210> SEQ ID NO 11
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
```

```
<222> LOCATION: 1..19
<223> OTHER INFORMATION: /mod_base = "2'-hydroxy corresponding base"

<400> SEQUENCE: 11
gcgaaggagg cgagacacct t                                              21

<210> SEQ ID NO 12
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 12
aggcgagaca cccacuucct t                                              21

<210> SEQ ID NO 13
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 13
ugucacucgg ucccagacat t                                              21

<210> SEQ ID NO 14
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 14
caagacguag aaccuaccut t                                              21

<210> SEQ ID NO 15
<211> LENGTH: 21
<212> TYPE: DNA
```

```
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 15
ucacucgguc ccagacacct t                                             21

<210> SEQ ID NO 16
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 16
ccacaacaga cgggacaact t                                             21

<210> SEQ ID NO 17
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 17
caacagacgg gacaacuugt t                                             21

<210> SEQ ID NO 18
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
```

-continued

```
<221> NAME/KEY: modified_base
<222> LOCATION: 1..19
<223> OTHER INFORMATION: /mod_base = "2'-hydroxy corresponding base"

<400> SEQUENCE: 18
aagacguaga accuaccugt t                                              21

<210> SEQ ID NO 19
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 19
auguuccaga ggcgaaggat t                                              21

<210> SEQ ID NO 20
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 20
ccauguucca gaggcgaagt t                                              21

<210> SEQ ID NO 21
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 21
cauguuccag aggcgaaggt t                                              21

<210> SEQ ID NO 22
<211> LENGTH: 21
```

```
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 22
cugcaagacg uagaaccuat t                                              21

<210> SEQ ID NO 23
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 23
acguagaacc uaccugccct t                                              21

<210> SEQ ID NO 24
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 24
ugucaucgau caaagugugt t                                              21

<210> SEQ ID NO 25
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 25
agacagacgg cacgauggct t                                              21

<210> SEQ ID NO 26
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 26
ugaccagugg cucuguuuut t                                              21

<210> SEQ ID NO 27
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 27
cggcacgaug gcacugagct t                                              21

<210> SEQ ID NO 28
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 28
ugcugucauc gaucaaagut t                                              21

<210> SEQ ID NO 29
```

```
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 29
gaacauaggu cuuggaauat t                                        21

<210> SEQ ID NO 30
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 30
ggcugcuguc aucgaucaat t                                        21

<210> SEQ ID NO 31
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 31
cugcugucau cgaucaaagt t                                        21

<210> SEQ ID NO 32
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
```

```
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 32
gcggcugcug ucaucgauct t                                              21

<210> SEQ ID NO 33
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 33
gcugucaucg aucaaagugt t                                              21

<210> SEQ ID NO 34
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 34
cugucaucga ucaaagugut t                                              21

<210> SEQ ID NO 35
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 35
gucaucgauc aaaguguggt t                                              21
```

```
<210> SEQ ID NO 36
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 36
acaacagacg ggacaacuut t                                              21

<210> SEQ ID NO 37
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 37
ccaagaccua uguucugggt t                                              21

<210> SEQ ID NO 38
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 38
uuugaucgau gacagcagct t                                              21

<210> SEQ ID NO 39
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
```

```
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 39
aguugucccg ucuguugugt t                                              21

<210> SEQ ID NO 40
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 40
caucgugccg ucugucuggt t                                              21

<210> SEQ ID NO 41
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 41
gguucuacgu cuugcagcat t                                              21

<210> SEQ ID NO 42
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 42
ugggugucuc gccuccuuct t                                              21
```

<210> SEQ ID NO 43
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 43
guagguucua cgucuugcat t                                              21

<210> SEQ ID NO 44
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 44
ugcaaguugu cccgucugut t                                              21

<210> SEQ ID NO 45
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 45
ucccacacuu ugaucgaugt t                                              21

<210> SEQ ID NO 46
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:

```
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 46
ccaucgugcc gucugucugt t                                              21

<210> SEQ ID NO 47
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 47
ggugucucgc cuccuucgct t                                              21

<210> SEQ ID NO 48
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 48
ggaagugggu gucucgccut t                                              21

<210> SEQ ID NO 49
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 49 ugucuggac cgagugacat t                                               21
```

```
<210> SEQ ID NO 50
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 50
agguagguuc uacgucuugt t                                              21

<210> SEQ ID NO 51
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 51
ggugucuggg accgagugat t                                              21

<210> SEQ ID NO 52
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 52
guugucccgu cuguuguggt t                                              21

<210> SEQ ID NO 53
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 53
caaguugucc cgucuguugt t                                              21

<210> SEQ ID NO 54
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 54
cagguagguu cuacgucuut t                                              21

<210> SEQ ID NO 55
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 55
uccuucgccu cuggaacaut t                                              21

<210> SEQ ID NO 56
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 56
```

-continued cuucgccucu ggaacauggt t                                              21

<210> SEQ ID NO 57
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 57
ccuucgccuc uggaacaugt t                                              21

<210> SEQ ID NO 58
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 58
uagguucuac gucuugcagt t                                              21

<210> SEQ ID NO 59
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 59
gggcagguag guucuacgut t                                              21

<210> SEQ ID NO 60
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.

-continued

```
    base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 60
cacacuuuga ucgaugacat t                                                21

<210> SEQ ID NO 61
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 61
gccaucgugc cgucugucut t                                                21

<210> SEQ ID NO 62
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 62
aaaacagagc cacuggucat t                                                21

<210> SEQ ID NO 63
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 63
```
gcucagugcc aucgugccgt t         21

<210> SEQ ID NO 64
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 64
acuuugaucg augacagcat t         21

<210> SEQ ID NO 65
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 65
uauuccaaga ccuauguuct t         21

<210> SEQ ID NO 66
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 66
uugaucgaug acagcagcct t         21

<210> SEQ ID NO 67
<211> LENGTH: 21
<212> TYPE: DNA
<213> ORGANISM: Artificial sequence
<220> FEATURE:
<223> OTHER INFORMATION: siRNAs targeting hamp
<220> FEATURE:

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 67
cuuugaucga ugacagcagt t                                              21

<210> SEQ ID NO 68
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 68
gaucgaugac agcagccgct t                                              21

<210> SEQ ID NO 69
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 69
cacuuugauc gaugacagct t                                              21

<210> SEQ ID NO 70
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 70
acacuuugau cgaugacagt t                                              21

<210> SEQ ID NO 71
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 71
ccacacuuug aucgaugact t                                              21

<210> SEQ ID NO 72
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 72
aaguugcccc gucuguugut t                                              21

<210> SEQ ID NO 73
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 73
cagacauugc gauaccaaut t                                              21

<210> SEQ ID NO 74
<211> LENGTH: 21
<212> TYPE: DNA
<213> ORGANISM: Artificial sequence
<220> FEATURE:
<223> OTHER INFORMATION: siRNAs targeting hamp
```

-continued

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 5, 7, 8, 10, 13, 15, 16, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 6, 9, 11, 12, 14, 17, 18
<223> OTHER INFORMATION: /mod_base = "2'-hydroxy corresponding base"

<400> SEQUENCE: 74
cagacauugc gauaccaaut t                                              21

<210> SEQ ID NO 75
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 5, 7, 8, 10, 13, 15, 16, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 6, 9, 11, 12, 14, 17, 18
<223> OTHER INFORMATION: /mod_base = "2'-hydroxy corresponding base"

<400> SEQUENCE: 75
cagacauugc gauaccaaut t                                              21

<210> SEQ ID NO 76
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 76
agacauugcg auaccaaugt t                                              21

<210> SEQ ID NO 77
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
```

-continued

```
<220> FEATURE:
<221> NAME/KEY: modified_base
<222> LOCATION: 4, 6, 7, 9, 12, 14, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 8, 10, 11, 13, 16, 17, 19
<223> OTHER INFORMATION: /mod_base = "2'-hydroxy corresponding base"

<400> SEQUENCE: 77
agacauugcg auaccaaugt t                                              21

<210> SEQ ID NO 78
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 6, 7, 9, 12, 14, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 8, 10, 11, 13, 16, 17, 19
<223> OTHER INFORMATION: /mod_base = "2'-hydroxy corresponding base"

<400> SEQUENCE: 78
agacauugcg auaccaaugt t                                              21

<210> SEQ ID NO 79
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 79
gcagacauug cgauaccaat t                                              21

<210> SEQ ID NO 80
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 6, 8, 9, 11, 14, 16, 17
```

```
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 7, 10, 12, 13, 15, 18, 19
<223> OTHER INFORMATION: /mod_base = "2'-hydroxy corresponding base"

<400> SEQUENCE: 80
gcagacauug cgauaccaat t                                              21

<210> SEQ ID NO 81
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 6, 8, 9, 11, 14, 16, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 7, 10, 12, 13, 15, 18, 19
<223> OTHER INFORMATION: /mod_base = "2'-hydroxy corresponding base"

<400> SEQUENCE: 81
gcagacauug cgauaccaat t                                              21

<210> SEQ ID NO 82
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 82
uagccuagag ccacauccut t                                              21

<210> SEQ ID NO 83
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 5, 6, 11, 12, 14, 16, 17, 18, 19
<223> OTHER INFORMATION: /mod_base = "2'-O-methyl corresponding base"
<220> FEATURE:
<221> NAME/KEY: modified_base
```

```
<222> LOCATION: 21
<223> OTHER INFORMATION: /mod_base = "5'-thio thymidine"
<220> FEATURE:
<221> NAME/KEY: modified_base
<222> LOCATION: 2, 3, 7, 8, 9, 10, 13, 15
<223> OTHER INFORMATION: /mod_base = "2'-hydroxy corresponding base"

<400> SEQUENCE: 83
uagccuagag ccacauccut t                                            21

<210> SEQ ID NO 84
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 5, 6, 11, 12, 14, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 7, 8, 9, 10, 13, 15
<223> OTHER INFORMATION: /mod_base = "2'-hydroxy corresponding base"

<400> SEQUENCE: 84
uagccuagag ccacauccut t                                            21

<210> SEQ ID NO 85
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 85
gacauugcga uaccaaugct t                                            21

<210> SEQ ID NO 86
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 5, 6, 8, 11, 13, 14, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
```

```
<221> NAME/KEY: modified_base
<222> LOCATION: 1, 2, 4, 7, 9, 10, 12, 15, 16, 18
<223> OTHER INFORMATION: /mod_base = "2'-hydroxy corresponding base"

<400> SEQUENCE: 86
gacauugcga uaccaaugct t                                              21

<210> SEQ ID NO 87
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 5, 6, 8, 11, 13, 14, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 7, 9, 10, 12, 15, 16, 18
<223> OTHER INFORMATION: /mod_base = "2'-hydroxy corresponding base"

<400> SEQUENCE: 87
gacauugcga uaccaaugct t                                              21

<210> SEQ ID NO 88
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 88
uugcgauacc aaugcagaat t                                              21

<210> SEQ ID NO 89
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 7, 9, 10, 13, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 5, 6, 8, 11, 12, 14, 16, 17, 18, 19
<223> OTHER INFORMATION: /mod_base = "2'-hydroxy corresponding base"
```

```
<400> SEQUENCE: 89
uugcgauacc aaugcagaat t                                              21

<210> SEQ ID NO 90
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 7, 9, 10, 13, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 5, 6, 8, 11, 12, 14, 16, 17, 18, 19
<223> OTHER INFORMATION: /mod_base = "2'-hydroxy corresponding base"

<400> SEQUENCE: 90
uugcgauacc aaugcagaat t                                              21

<210> SEQ ID NO 91
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 91
ugcgauacca augcagaagt t                                              21

<210> SEQ ID NO 92
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 6, 8, 9, 12, 14
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 4, 5, 7, 10, 11, 13, 15, 16, 17, 18, 19
<223> OTHER INFORMATION: /mod_base = "2'-hydroxy corresponding base"

<400> SEQUENCE: 92
```
ugcgauacca augcagaagt t                                              21

<210> SEQ ID NO 93
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 6, 8, 9, 12, 14
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 4, 5, 7, 10, 11, 13, 15, 16, 17, 18, 19
<223> OTHER INFORMATION: /mod_base = "2'-hydroxy corresponding base"

<400> SEQUENCE: 93
ugcgauacca augcagaagt t                                              21

<210> SEQ ID NO 94
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 94
caccaccuau cuccaucaat t                                              21

<210> SEQ ID NO 95
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 6, 7, 8, 10, 11, 12, 13, 14, 16, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 5, 9, 15, 18, 19
<223> OTHER INFORMATION: /mod_base = "2'-hydroxy corresponding base"

<400> SEQUENCE: 95
caccaccuau cuccaucaat t                                              21

-continued

```
<210> SEQ ID NO 96
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 6, 7, 8, 10, 11, 12, 13, 14, 16, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 5, 9, 15, 18, 19
<223> OTHER INFORMATION: /mod_base = "2'-hydroxy corresponding base"

<400> SEQUENCE: 96
caccaccuau cuccaucaat t                                              21

<210> SEQ ID NO 97
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 97
agaugagaca gacuacagat t                                              21

<210> SEQ ID NO 98
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 9, 13, 14, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 7, 8, 10, 11, 12, 15, 17, 18, 19
<223> OTHER INFORMATION: /mod_base = "2'-hydroxy corresponding base"

<400> SEQUENCE: 98
agaugagaca gacuacagat t                                              21

<210> SEQ ID NO 99
<211> LENGTH: 21
<212> TYPE: DNA
```

```
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 9, 13, 14, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 7, 8, 10, 11, 12, 15, 17, 18, 19
<223> OTHER INFORMATION: /mod_base = "2'-hydroxy corresponding base"

<400> SEQUENCE: 99
agaugagaca gacuacagat t                                              21

<210> SEQ ID NO 100
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 100
auugcgauac caaugcagat t                                              21

<210> SEQ ID NO 101
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 5, 8, 10, 11, 14, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 4, 6, 7, 9, 12, 13, 15, 17, 18, 19
<223> OTHER INFORMATION: /mod_base = "2'-hydroxy corresponding base"

<400> SEQUENCE: 101
auugcgauac caaugcagat t                                              21

<210> SEQ ID NO 102
<211> LENGTH: 21
<212> TYPE: DNA
<213> ORGANISM: Artificial sequence
<220> FEATURE:
<223> OTHER INFORMATION: siRNAs targeting hamp
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 5, 8, 10, 11, 14, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 4, 6, 7, 9, 12, 13, 15, 17, 18, 19
<223> OTHER INFORMATION: /mod_base = "2'-hydroxy corresponding base"

<400> SEQUENCE: 102
auugcgauac caaugcagat t                                              21

<210> SEQ ID NO 103
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 103
aauaaagacg auuuuauuut t                                              21

<210> SEQ ID NO 104
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 9, 12, 13, 14, 15, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 5, 6, 7, 8, 10, 11, 16
<223> OTHER INFORMATION: /mod_base = "2'-hydroxy corresponding base"

<400> SEQUENCE: 104
aauaaagacg auuuuauuut t                                              21

<210> SEQ ID NO 105
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 3, 9, 12, 13, 14, 15, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 5, 6, 7, 8, 10, 11, 16
<223> OTHER INFORMATION: /mod_base = "2'-hydroxy corresponding base"

<400> SEQUENCE: 105
aauaaagacg auuuuauuut t                                              21

<210> SEQ ID NO 106
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 106
ggcagacauu gcgauaccat t                                              21

<210> SEQ ID NO 107
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 7, 9, 10, 12, 15, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 5, 6, 8, 11, 13, 14, 16, 19
<223> OTHER INFORMATION: /mod_base = "2'-hydroxy corresponding base"

<400> SEQUENCE: 107
ggcagacauu gcgauaccat t                                              21

<210> SEQ ID NO 108
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 7, 9, 10, 12, 15, 17, 18
```

```
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 5, 6, 8, 11, 13, 14, 16, 19
<223> OTHER INFORMATION: /mod_base = "2'-hydroxy corresponding base"

<400> SEQUENCE: 108
ggcagacauu gcgauaccat t                                              21

<210> SEQ ID NO 109
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 109
ugcuguaaca auucccagut t                                              21

<210> SEQ ID NO 110
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 6, 9, 12, 13, 14, 15, 16, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 5, 7, 8, 10, 11, 17, 18
<223> OTHER INFORMATION: /mod_base = "2'-hydroxy corresponding base"

<400> SEQUENCE: 110
ugcuguaaca auucccagut t                                              21

<210> SEQ ID NO 111
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 6, 9, 12, 13, 14, 15, 16, 19
<223> OTHER INFORMATION: /mod_base = "2'-O-methyl corresponding base"
<220> FEATURE:
<221> NAME/KEY: modified_base
```

```
<222> LOCATION: 21
<223> OTHER INFORMATION: /mod_base = "5'-thio thymidine"
<220> FEATURE:
<221> NAME/KEY: modified_base
<222> LOCATION: 2, 5, 7, 8, 10, 11, 17, 18
<223> OTHER INFORMATION: /mod_base = "2'-hydroxy corresponding base"

<400> SEQUENCE: 111
ugcuguaaca auucccagut t                                              21

<210> SEQ ID NO 112
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 112
ucuucugcug uaaaugcugt t                                              21

<210> SEQ ID NO 113
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 5, 6, 8, 9, 11, 15, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 7, 10, 12, 13, 14, 16, 19
<223> OTHER INFORMATION: /mod_base = "2'-hydroxy corresponding base"

<400> SEQUENCE: 113
ucuucugcug uaaaugcugt t                                              21

<210> SEQ ID NO 114
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 5, 6, 8, 9, 11, 15, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
```

```
<221> NAME/KEY: modified_base
<222> LOCATION: 7, 10, 12, 13, 14, 16, 19
<223> OTHER INFORMATION: /mod_base = "2'-hydroxy corresponding base"

<400> SEQUENCE: 114
ucuucugcug uaaaugcugt t                                              21

<210> SEQ ID NO 115
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 115
cugccugucu ccugcuucut t                                              21

<210> SEQ ID NO 116
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 5, 6, 8, 9, 10, 11, 12, 13, 15, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 7, 14
<223> OTHER INFORMATION: /mod_base = "2'-hydroxy corresponding base"

<400> SEQUENCE: 116
cugccugucu ccugcuucut t                                              21

<210> SEQ ID NO 117
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 5, 6, 8, 9, 10, 11, 12, 13, 15, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 7, 14
<223> OTHER INFORMATION: /mod_base = "2'-hydroxy corresponding base"
```

-continued

<400> SEQUENCE: 117
cugccugucu ccugcuucut t                                              21

<210> SEQ ID NO 118
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 118
ugccugucuc cugcuucuct t                                              21

<210> SEQ ID NO 119
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 5, 7, 8, 9, 10, 11, 12, 14, 15, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 6, 13
<223> OTHER INFORMATION: /mod_base = "2'-hydroxy corresponding base"

<400> SEQUENCE: 119
ugccugucuc cugcuucuct t                                              21

<210> SEQ ID NO 120
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 5, 7, 8, 9, 10, 11, 12, 14, 15, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 6, 13
<223> OTHER INFORMATION: /mod_base = "2'-hydroxy corresponding base"

<400> SEQUENCE: 120
ugccugucuc cugcuucuct t                                              21

<210> SEQ ID NO 121
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 121
gcugccuguc uccugcuuct t                                              21

<210> SEQ ID NO 122
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 5, 6, 7, 9, 10, 11, 12, 13, 14, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 4, 8, 15
<223> OTHER INFORMATION: /mod_base = "2'-hydroxy corresponding base"

<400> SEQUENCE: 122
gcugccuguc uccugcuuct t                                              21

<210> SEQ ID NO 123
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 5, 6, 7, 9, 10, 11, 12, 13, 14, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 4, 8, 15
<223> OTHER INFORMATION: /mod_base = "2'-hydroxy corresponding base"

<400> SEQUENCE: 123
gcugccuguc uccugcuuct t                                              21

```
<210> SEQ ID NO 124
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 124
gccugucucc ugcuucucct t                                              21

<210> SEQ ID NO 125
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 4, 6, 7, 8, 9, 10, 11, 13, 14, 15, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 5, 12
<223> OTHER INFORMATION: /mod_base = "2'-hydroxy corresponding base"

<400> SEQUENCE: 125
gccugucucc ugcuucucct t                                              21

<210> SEQ ID NO 126
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 4, 6, 7, 8, 9, 10, 11, 13, 14, 15, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 5, 12
<223> OTHER INFORMATION: /mod_base = "2'-hydroxy corresponding base"

<400> SEQUENCE: 126
gccugucucc ugcuucucct t                                              21

<210> SEQ ID NO 127
<211> LENGTH: 21
<212> TYPE: DNA
```

```
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 127
caggcugccu gucuccugct t                                              21

<210> SEQ ID NO 128
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 5, 6, 8, 9, 10, 12, 13, 14, 15, 16, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 7, 11, 18
<223> OTHER INFORMATION: /mod_base = "2'-hydroxy corresponding base"

<400> SEQUENCE: 128
caggcugccu gucuccugct t                                              21

<210> SEQ ID NO 129
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 5, 6, 8, 9, 10, 12, 13, 14, 15, 16, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 7, 11, 18
<223> OTHER INFORMATION: /mod_base = "2'-hydroxy corresponding base"

<400> SEQUENCE: 129
caggcugccu gucuccugct t                                              21

<210> SEQ ID NO 130
<211> LENGTH: 21
<212> TYPE: DNA
<213> ORGANISM: Artificial sequence
<220> FEATURE:
<223> OTHER INFORMATION: siRNAs targeting hamp
```

-continued

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 130
cuucugcugu aaaugcugut t                                              21

<210> SEQ ID NO 131
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 5, 7, 8, 10, 14, 16, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 6, 9, 11, 12, 13, 15, 18
<223> OTHER INFORMATION: /mod_base = "2'-hydroxy corresponding base"

<400> SEQUENCE: 131
cuucugcugu aaaugcugut t                                              21

<210> SEQ ID NO 132
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 5, 7, 8, 10, 14, 16, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 6, 9, 11, 12, 13, 15, 18
<223> OTHER INFORMATION: /mod_base = "2'-hydroxy corresponding base"

<400> SEQUENCE: 132
cuucugcugu aaaugcugut t                                              21

<210> SEQ ID NO 133
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 133
uucugcugua aaugcuguat t                                              21

<210> SEQ ID NO 134
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 6, 7, 9, 13, 15, 16, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 5, 8, 10, 11, 12, 14, 17, 19
<223> OTHER INFORMATION: /mod_base = "2'-hydroxy corresponding base"

<400> SEQUENCE: 134
uucugcugua aaugcuguat t                                              21

<210> SEQ ID NO 135
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 6, 7, 9, 13, 15, 16, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 5, 8, 10, 11, 12, 14, 17, 19
<223> OTHER INFORMATION: /mod_base = "2'-hydroxy corresponding base"

<400> SEQUENCE: 135
uucugcugua aaugcuguat t                                              21

<210> SEQ ID NO 136
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
```

```
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 136
ucugcuguaa augcuguaat t                                               21

<210> SEQ ID NO 137
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 5, 6, 8, 12, 14, 15, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 4, 7, 9, 10, 11, 13, 16, 18, 19
<223> OTHER INFORMATION: /mod_base = "2'-hydroxy corresponding base"

<400> SEQUENCE: 137
ucugcuguaa augcuguaat t                                               21

<210> SEQ ID NO 138
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 5, 6, 8, 12, 14, 15, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 4, 7, 9, 10, 11, 13, 16, 18, 19
<223> OTHER INFORMATION: /mod_base = "2'-hydroxy corresponding base"

<400> SEQUENCE: 138
ucugcuguaa augcuguaat t                                               21

<210> SEQ ID NO 139
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
```

```
<222> LOCATION: 1..19
<223> OTHER INFORMATION: /mod_base = "2'-hydroxy corresponding base"

<400> SEQUENCE: 139
aggcugccug ucuccugcut t                                              21

<210> SEQ ID NO 140
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 5, 7, 8, 9, 11, 12, 13, 14, 15, 16, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 6, 10, 17
<223> OTHER INFORMATION: /mod_base = "2'-hydroxy corresponding base"

<400> SEQUENCE: 140
aggcugccug ucuccugcut t                                              21

<210> SEQ ID NO 141
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 5, 7, 8, 9, 11, 12, 13, 14, 15, 16, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 6, 10, 17
<223> OTHER INFORMATION: /mod_base = "2'-hydroxy corresponding base"

<400> SEQUENCE: 141
aggcugccug ucuccugcut t                                              21

<210> SEQ ID NO 142
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 142
ggcugccugu cuccugcuut t                                              21

<210> SEQ ID NO 143
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 6, 7, 8, 10, 11, 12, 13, 14, 15, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 5, 9, 16
<223> OTHER INFORMATION: /mod_base = "2'-hydroxy corresponding base"

<400> SEQUENCE: 143
ggcugccugu cuccugcuut t                                              21

<210> SEQ ID NO 144
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 6, 7, 8, 10, 11, 12, 13, 14, 15, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 5, 9, 16
<223> OTHER INFORMATION: /mod_base = "2'-hydroxy corresponding base"

<400> SEQUENCE: 144
ggcugccugu cuccugcuut t                                              21

<210> SEQ ID NO 145
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 145
auugguaucg caaugucugt t                                              21
```

```
<210> SEQ ID NO 146
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 6, 11
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 7, 8, 9, 10, 12, 13, 14, 15, 16, 17, 18,
      19
<223> OTHER INFORMATION: /mod_base = "2'-hydroxy corresponding base"

<400> SEQUENCE: 146
auugguaucg caaugucugt t                                              21

<210> SEQ ID NO 147
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 6, 11, 14, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 4, 5, 7, 8, 9, 10, 12, 13, 15, 16, 17, 19
<223> OTHER INFORMATION: /mod_base = "2'-hydroxy corresponding base"

<400> SEQUENCE: 147
auugguaucg caaugucugt t                                              21

<210> SEQ ID NO 148
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 148
cauugguauc gcaaugucut t                                              21
```

```
<210> SEQ ID NO 149
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 7, 12
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 5, 6, 8, 9, 10, 11, 13, 14, 15, 16, 17, 18, 19
<223> OTHER INFORMATION: /mod_base = "2'-hydroxy corresponding base"

<400> SEQUENCE: 149
cauugguauc gcaaugucut t                                              21

<210> SEQ ID NO 150
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 7, 12, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 5, 6, 8, 9, 10, 11, 13, 14, 16, 17, 18, 19
<223> OTHER INFORMATION: /mod_base = "2'-hydroxy corresponding base"

<400> SEQUENCE: 150
cauugguauc gcaaugucut t                                              21

<210> SEQ ID NO 151
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 151
uugguaucgc aaugucugct t                                              21

<210> SEQ ID NO 152
<211> LENGTH: 21
<212> TYPE: DNA
```

```
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 10
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 6, 7, 8, 9, 11, 12, 13, 14, 15, 16, 17, 18,
      19
<223> OTHER INFORMATION: /mod_base = "2'-hydroxy corresponding base"

<400> SEQUENCE: 152
uugguaucgc aaugucugct t                                              21

<210> SEQ ID NO 153
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 5, 10, 13, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 4, 6, 7, 8, 9, 11, 12, 14, 15, 16, 18, 19
<223> OTHER INFORMATION: /mod_base = "2'-hydroxy corresponding base"

<400> SEQUENCE: 153
uugguaucgc aaugucugct t                                              21

<210> SEQ ID NO 154
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 154
aggauguggc ucuaggcuat t                                              21

<210> SEQ ID NO 155
<211> LENGTH: 21
<212> TYPE: DNA
<213> ORGANISM: Artificial sequence
<220> FEATURE:
```

```
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 13, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 11, 12, 14, 15, 16, 17,
      19
<223> OTHER INFORMATION: /mod_base = "2'-hydroxy corresponding base"

<400> SEQUENCE: 155
aggauguggc ucuaggcuat t                                              21

<210> SEQ ID NO 156
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 7, 13, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 6, 8, 9, 10, 11, 12, 14, 15, 16, 17, 19
<223> OTHER INFORMATION: /mod_base = "2'-hydroxy corresponding base"

<400> SEQUENCE: 156
aggauguggc ucuaggcuat t                                              21

<210> SEQ ID NO 157
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 157
gcauugguau cgcaauguct t                                              21

<210> SEQ ID NO 158
<211> LENGTH: 21
<212> TYPE: DNA
<213> ORGANISM: Artificial sequence
<220> FEATURE:
<223> OTHER INFORMATION: siRNAs targeting hamp
<220> FEATURE:
```

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 8, 13
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 6, 7, 9, 10, 11, 12, 14, 15, 16, 17, 18, 19
<223> OTHER INFORMATION: /mod_base = "2'-hydroxy corresponding base"

<400> SEQUENCE: 158
gcauugguau cgcaauguct t                                              21

<210> SEQ ID NO 159
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 4, 5, 8, 13, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 6, 7, 9, 10, 11, 12, 14, 15, 17, 18, 19
<223> OTHER INFORMATION: /mod_base = "2'-hydroxy corresponding base"

<400> SEQUENCE: 159
gcauugguau cgcaauguct t                                              21

<210> SEQ ID NO 160
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 160
uucugcauug guaucgcaat t                                              21

<210> SEQ ID NO 161
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
```

-continued

```
<221> NAME/KEY: modified_base
<222> LOCATION: 6, 12, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 7, 8, 9, 10, 11, 13, 14, 15, 16, 18, 19
<223> OTHER INFORMATION: /mod_base = "2'-hydroxy corresponding base"

<400> SEQUENCE: 161
uucugcauug guaucgcaat t                                              21

<210> SEQ ID NO 162
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 6, 8, 9, 12, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 5, 7, 10, 11, 13, 14, 15, 16, 18, 19
<223> OTHER INFORMATION: /mod_base = "2'-hydroxy corresponding base"

<400> SEQUENCE: 162
uucugcauug guaucgcaat t                                              21

<210> SEQ ID NO 163
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 163
cuucugcauu gguaucgcat t                                              21

<210> SEQ ID NO 164
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 7, 13, 18
<223> OTHER INFORMATION: /mod_base = "2'-O-methyl corresponding base"
```

```
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 8, 9, 10, 11, 12, 14, 15, 16, 17, 19
<223> OTHER INFORMATION: /mod_base = "2'-hydroxy corresponding base"

<400> SEQUENCE: 164
cuucugcauu gguaucgcat t                                              21

<210> SEQ ID NO 165
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 5, 7, 9, 10, 13, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 6, 8, 11, 12, 14, 15, 16, 17, 19
<223> OTHER INFORMATION: /mod_base = "2'-hydroxy corresponding base"

<400> SEQUENCE: 165
cuucugcauu gguaucgcat t                                              21

<210> SEQ ID NO 166
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 166
uugauggaga uagguggugt t                                              21

<210> SEQ ID NO 167
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 11
<223> OTHER INFORMATION: /mod_base = "2'-O-methyl corresponding base"
<220> FEATURE:
<221> NAME/KEY: modified_base
<222> LOCATION: 21
```

<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 12, 13, 14, 15, 16, 17,
      18, 19
<223> OTHER INFORMATION: /mod_base = "2'-hydroxy corresponding base"

<400> SEQUENCE: 167
uugauggaga uagguggugt t                                              21

<210> SEQ ID NO 168
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 5, 11, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 4, 6, 7, 8, 9, 10, 12, 13, 14, 16, 17, 19
<223> OTHER INFORMATION: /mod_base = "2'-hydroxy corresponding base"

<400> SEQUENCE: 168
uugauggaga uagguggugt t                                              21

<210> SEQ ID NO 169
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 169
ucuguagucu gucucaucut t                                              21

<210> SEQ ID NO 170
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:

```
<221> NAME/KEY: modified_base
<222> LOCATION: 1, 2, 3, 4, 6, 7, 8, 9, 10, 11, 12, 13, 14, 16, 17, 18,
      19
<223> OTHER INFORMATION: /mod_base = "2'-hydroxy corresponding base"

<400> SEQUENCE: 170
ucuguagucu gucucaucut t                                              21

<210> SEQ ID NO 171
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 5, 10, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 6, 7, 8, 9, 11, 12, 13, 14, 16, 17, 18, 19
<223> OTHER INFORMATION: /mod_base = "2'-hydroxy corresponding base"

<400> SEQUENCE: 171
ucuguagucu gucucaucut t                                              21

<210> SEQ ID NO 172
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 172
ucugcauugg uaucgcaaut t                                              21

<210> SEQ ID NO 173
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 11, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 6, 7, 8, 9, 10, 12, 13, 14, 15, 17, 18, 19
```

```
<223> OTHER INFORMATION: /mod_base = "2'-hydroxy corresponding base"

<400> SEQUENCE: 173
ucugcauugg uaucgcaaut t                                              21

<210> SEQ ID NO 174
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 5, 7, 8, 11, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 6, 9, 10, 12, 13, 14, 15, 17, 18, 19
<223> OTHER INFORMATION: /mod_base = "2'-hydroxy corresponding base"

<400> SEQUENCE: 174
ucugcauugg uaucgcaaut t                                              21

<210> SEQ ID NO 175
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 175
aaauaaaauc gucuuuauut t                                              21

<210> SEQ ID NO 176
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 7, 8, 9, 10, 11, 12, 13, 14, 15, 17, 18,
      19
<223> OTHER INFORMATION: /mod_base = "2'-hydroxy corresponding base"
```

<400> SEQUENCE: 176
aaauaaaauc gucuuuauut t                                              21

<210> SEQ ID NO 177
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 14, 15, 16, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 7, 8, 9, 10, 11, 12, 13, 17, 19
<223> OTHER INFORMATION: /mod_base = "2'-hydroxy corresponding base"

<400> SEQUENCE: 177
aaauaaaauc gucuuuauut t                                              21

<210> SEQ ID NO 178
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 178
ugguaucgca augucugcct t                                              21

<210> SEQ ID NO 179
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 9
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 7, 8, 10, 11, 12, 13, 14, 15, 16, 17, 18,
      19
<223> OTHER INFORMATION: /mod_base = "2'-hydroxy corresponding base"

<400> SEQUENCE: 179
ugguaucgca augucugcct t                                          21

<210> SEQ ID NO 180
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 9, 12, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 5, 6, 7, 8, 10, 11, 13, 14, 15, 17, 18, 19
<223> OTHER INFORMATION: /mod_base = "2'-hydroxy corresponding base"

<400> SEQUENCE: 180
ugguaucgca augucugcct t                                          21

<210> SEQ ID NO 181
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 181
acugggaauu guuacagcat t                                          21

<210> SEQ ID NO 182
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 13, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 9, 10, 11, 12, 14, 16, 17, 19
<223> OTHER INFORMATION: /mod_base = "2'-hydroxy corresponding base"

<400> SEQUENCE: 182
acugggaauu guuacagcat t                                          21

-continued

```
<210> SEQ ID NO 183
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 9, 10, 12, 13, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 5, 6, 7, 8, 11, 14, 16, 17, 19
<223> OTHER INFORMATION: /mod_base = "2'-hydroxy corresponding base"

<400> SEQUENCE: 183
acugggaauu guuacagcat t                                              21

<210> SEQ ID NO 184
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 184
cagcauuuac agcagaagat t                                              21

<210> SEQ ID NO 185
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 8, 10, 13
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 5, 6, 7, 9, 11, 12, 14, 15, 16, 17, 18, 19
<223> OTHER INFORMATION: /mod_base = "2'-hydroxy corresponding base"

<400> SEQUENCE: 185
cagcauuuac agcagaagat t                                              21

<210> SEQ ID NO 186
<211> LENGTH: 21
<212> TYPE: DNA
```

```
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 6, 7, 8, 10, 13
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 5, 9, 11, 12, 14, 15, 16, 17, 18, 19
<223> OTHER INFORMATION: /mod_base = "2'-hydroxy corresponding base"

<400> SEQUENCE: 186
cagcauuuac agcagaagat t                                          21

<210> SEQ ID NO 187
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 187
agaagcagga gacaggcagt t                                          21

<210> SEQ ID NO 188
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 6, 13, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 7, 8, 9, 10, 11, 12, 14, 15, 16, 18, 19
<223> OTHER INFORMATION: /mod_base = "2'-hydroxy corresponding base"

<400> SEQUENCE: 188
agaagcagga gacaggcagt t                                          21

<210> SEQ ID NO 189
<211> LENGTH: 21
<212> TYPE: DNA
<213> ORGANISM: Artificial sequence
<220> FEATURE:
<223> OTHER INFORMATION: siRNAs targeting hamp
```

-continued

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 6, 13, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 7, 8, 9, 10, 11, 12, 14, 15, 16, 18, 19
<223> OTHER INFORMATION: /mod_base = "2'-hydroxy corresponding base"

<400> SEQUENCE: 189
agaagcagga gacaggcagt t                                              21

<210> SEQ ID NO 190
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 190
gagaagcagg agacaggcat t                                              21

<210> SEQ ID NO 191
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 7, 14, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 8, 9, 10, 11, 12, 13, 15, 16, 17, 19
<223> OTHER INFORMATION: /mod_base = "2'-hydroxy corresponding base"

<400> SEQUENCE: 191
gagaagcagg agacaggcat t                                              21

<210> SEQ ID NO 192
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 7, 14, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 8, 9, 10, 11, 12, 13, 15, 16, 17, 19
<223> OTHER INFORMATION: /mod_base = "2'-hydroxy corresponding base"

<400> SEQUENCE: 192
gagaagcagg agacaggcat t                                              21

<210> SEQ ID NO 193
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 193
gaagcaggag acaggcagct t                                              21

<210> SEQ ID NO 194
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 12, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 6, 7, 8, 9, 10, 11, 13, 14, 15, 17, 18, 19
<223> OTHER INFORMATION: /mod_base = "2'-hydroxy corresponding base"

<400> SEQUENCE: 194
gaagcaggag acaggcagct t                                              21

<210> SEQ ID NO 195
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 12, 16
```

-continued

```
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 6, 7, 8, 9, 10, 11, 13, 14, 15, 17, 18, 19
<223> OTHER INFORMATION: /mod_base = "2'-hydroxy corresponding base"

<400> SEQUENCE: 195
gaagcaggag acaggcagct t                                              21

<210> SEQ ID NO 196
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 196
ggagaagcag gagacaggct t                                              21

<210> SEQ ID NO 197
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 8, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 9, 10, 11, 12, 13, 14, 16, 17, 18,
      19
<223> OTHER INFORMATION: /mod_base = "2'-hydroxy corresponding base"

<400> SEQUENCE: 197
ggagaagcag gagacaggct t                                              21

<210> SEQ ID NO 198
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 8, 15
<223> OTHER INFORMATION: /mod_base = "2'-O-methyl corresponding base"
<220> FEATURE:
```

```
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 9, 10, 11, 12, 13, 14, 16, 17, 18,
      19
<223> OTHER INFORMATION: /mod_base = "2'-hydroxy corresponding base"

<400> SEQUENCE: 198
ggagaagcag gagacaggct t                                            21

<210> SEQ ID NO 199
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 199
gcaggagaca ggcagccugt t                                            21

<210> SEQ ID NO 200
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 9, 13
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 6, 7, 8, 10, 11, 12, 14, 15, 16, 17, 18, 19
<223> OTHER INFORMATION: /mod_base = "2'-hydroxy corresponding base"

<400> SEQUENCE: 200
gcaggagaca ggcagccugt t                                            21

<210> SEQ ID NO 201
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 9, 13, 18
<223> OTHER INFORMATION: /mod_base = "2'-O-methyl corresponding base"
<220> FEATURE:
<221> NAME/KEY: modified_base
<222> LOCATION: 21
```

-continued

```
<223> OTHER INFORMATION: /mod_base = "5'-thio thymidine"
<220> FEATURE:
<221> NAME/KEY: modified_base
<222> LOCATION: 1, 3, 4, 5, 6, 7, 8, 10, 11, 12, 14, 15, 16, 17, 19
<223> OTHER INFORMATION: /mod_base = "2'-hydroxy corresponding base"

<400> SEQUENCE: 201
gcaggagaca ggcagccugt t                                              21

<210> SEQ ID NO 202
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 202
acagcauuua cagcagaagt t                                              21

<210> SEQ ID NO 203
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 5, 9, 11, 14
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 6, 7, 8, 10, 12, 13, 15, 16, 17, 18, 19
<223> OTHER INFORMATION: /mod_base = "2'-hydroxy corresponding base"

<400> SEQUENCE: 203
acagcauuua cagcagaagt t                                              21

<210> SEQ ID NO 204
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 5, 7, 8, 9, 11, 14
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
```

```
<222> LOCATION: 1, 3, 4, 6, 10, 12, 13, 15, 16, 17, 18, 19
<223> OTHER INFORMATION: /mod_base = "2'-hydroxy corresponding base"

<400> SEQUENCE: 204
acagcauuua cagcagaagt t                                              21

<210> SEQ ID NO 205
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 205
uacagcauuu acagcagaat t                                              21

<210> SEQ ID NO 206
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 6, 10, 12, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 4, 5, 7, 8, 9, 11, 13, 14, 16, 17, 18, 19
<223> OTHER INFORMATION: /mod_base = "2'-hydroxy corresponding base"

<400> SEQUENCE: 206
uacagcauuu acagcagaat t                                              21

<210> SEQ ID NO 207
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 6, 8, 9, 10, 12, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 4, 5, 7, 11, 13, 14, 16, 17, 18, 19
<223> OTHER INFORMATION: /mod_base = "2'-hydroxy corresponding base"
```

<400> SEQUENCE: 207
uacagcauuu acagcagaat t								21

<210> SEQ ID NO 208
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 208
uuacagcauu uacagcagat t								21

<210> SEQ ID NO 209
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 4, 7, 11, 13, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 5, 6, 8, 9, 10, 12, 14, 15, 17, 18, 19
<223> OTHER INFORMATION: /mod_base = "2'-hydroxy corresponding base"

<400> SEQUENCE: 209
uuacagcauu uacagcagat t								21

<210> SEQ ID NO 210
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 7, 9, 10, 11, 13, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 5, 6, 8, 12, 14, 15, 17, 18, 19
<223> OTHER INFORMATION: /mod_base = "2'-hydroxy corresponding base"

<400> SEQUENCE: 210
uuacagcauu uacagcagat t								21

```
<210> SEQ ID NO 211
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 211
agcaggagac aggcagccut t                                              21

<210> SEQ ID NO 212
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 10, 14
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 5, 6, 7, 8, 9, 11, 12, 13, 15, 16, 17, 18, 19
<223> OTHER INFORMATION: /mod_base = "2'-hydroxy corresponding base"

<400> SEQUENCE: 212
agcaggagac aggcagccut t                                              21

<210> SEQ ID NO 213
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 10, 14, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 4, 5, 6, 7, 8, 9, 11, 12, 13, 15, 16, 18, 19
<223> OTHER INFORMATION: /mod_base = "2'-hydroxy corresponding base"

<400> SEQUENCE: 213
agcaggagac aggcagccut t                                              21

<210> SEQ ID NO 214
```

```
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 214
aagcaggaga caggcagcct t                                           21

<210> SEQ ID NO 215
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 11, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 7, 8, 9, 10, 12, 13, 14, 16, 17, 18, 19
<223> OTHER INFORMATION: /mod_base = "2'-hydroxy corresponding base"

<400> SEQUENCE: 215
aagcaggaga caggcagcct t                                           21

<210> SEQ ID NO 216
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 11, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 7, 8, 9, 10, 12, 13, 14, 16, 17, 19
<223> OTHER INFORMATION: /mod_base = "2'-hydroxy corresponding base"

<400> SEQUENCE: 216
aagcaggaga caggcagcct t                                           21

<210> SEQ ID NO 217
<211> LENGTH: 21
<212> TYPE: DNA
<213> ORGANISM: Artificial sequence
```

-continued

```
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 5, 6, 8, 9, 11, 12, 15, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 4, 7, 10, 13, 14, 17, 18, 19
<223> OTHER INFORMATION: /mod_base = "2'-hydroxy corresponding base"

<400> SEQUENCE: 217
gcugcuguca ucgaucaaat t                                              21

<210> SEQ ID NO 218
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 6, 10, 13, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 4, 5, 7, 8, 9, 11, 12, 14, 16, 17, 19
<223> OTHER INFORMATION: /mod_base = "2'-hydroxy corresponding base"

<400> SEQUENCE: 218
ccagacagac ggcacgaugt t                                              21

<210> SEQ ID NO 219
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 9, 14, 16, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 7, 8, 10, 11, 12, 13, 15, 19
<223> OTHER INFORMATION: /mod_base = "2'-hydroxy corresponding base"

<400> SEQUENCE: 219
gaaggaggcg agacacccat t                                              21

<210> SEQ ID NO 220
<211> LENGTH: 21
<212> TYPE: DNA
```

```
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 8, 10, 15, 16, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 4, 5, 6, 7, 9, 11, 12, 13, 14, 18
<223> OTHER INFORMATION: /mod_base = "2'-hydroxy corresponding base"

<400> SEQUENCE: 220
ugcaagacgu agaaccuact t                                              21

<210> SEQ ID NO 221
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 7, 8, 13, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 5, 6, 9, 10, 11, 12, 14, 16, 17, 18, 19
<223> OTHER INFORMATION: /mod_base = "2'-hydroxy corresponding base"

<400> SEQUENCE: 221
caucgaucaa agugugggat t                                              21

<210> SEQ ID NO 222
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 5, 9, 12, 14, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 6, 7, 8, 10, 11, 13, 15, 16, 18, 19
<223> OTHER INFORMATION: /mod_base = "2'-hydroxy corresponding base"

<400> SEQUENCE: 222
cagacagacg gcacgauggt t                                              21

<210> SEQ ID NO 223
<211> LENGTH: 21
```

```
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 9, 11, 12, 13, 15, 16, 17, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 7, 8, 10, 14
<223> OTHER INFORMATION: /mod_base = "2'-hydroxy corresponding base"

<400> SEQUENCE: 223
aggcgagaca cccacuucct t                                             21

<210> SEQ ID NO 224
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 9, 11, 16, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 5, 6, 7, 8, 10, 12, 13, 14, 15, 19
<223> OTHER INFORMATION: /mod_base = "2'-hydroxy corresponding base"

<400> SEQUENCE: 224
cugcaagacg uagaaccuat t                                             21

<210> SEQ ID NO 225
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 6, 9, 12, 14, 15, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 5, 7, 8, 10, 11, 13, 16, 17, 18
<223> OTHER INFORMATION: /mod_base = "2'-hydroxy corresponding base"

<400> SEQUENCE: 225
cggcacgaug gcacugagct t                                             21

<210> SEQ ID NO 226
```

```
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 6, 7, 9, 10, 13, 14, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 5, 8, 11, 12, 15, 16, 17, 18
<223> OTHER INFORMATION: /mod_base = "2'-hydroxy corresponding base"

<400> SEQUENCE: 226
ugcugucauc gaucaaagut t                                              21

<210> SEQ ID NO 227
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 6, 10, 11, 12, 13, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 7, 8, 9, 14, 15, 16, 17, 19
<223> OTHER INFORMATION: /mod_base = "2'-hydroxy corresponding base"

<400> SEQUENCE: 227
gaacauaggu cuuggaauat t                                              21

<210> SEQ ID NO 228
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 6, 7, 9, 10, 12, 13, 16, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 5, 8, 11, 14, 15, 18, 19
<223> OTHER INFORMATION: /mod_base = "2'-hydroxy corresponding base"

<400> SEQUENCE: 228
ggcugcuguc aucgaucaat t                                              21
```

```
<210> SEQ ID NO 229
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 5, 7, 8, 10, 11, 14, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 6, 9, 12, 13, 16, 17, 18, 19
<223> OTHER INFORMATION: /mod_base = "2'-hydroxy corresponding base"

<400> SEQUENCE: 229
cugcugucau cgaucaaagt t                                          21

<210> SEQ ID NO 230
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 5, 6, 8, 9, 11, 12, 14, 15, 18, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 7, 10, 13, 16, 17
<223> OTHER INFORMATION: /mod_base = "2'-hydroxy corresponding base"

<400> SEQUENCE: 230
gcggcugcug ucaucgauct t                                          21

<210> SEQ ID NO 231
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 5, 6, 8, 9, 12, 13, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 4, 7, 10, 11, 14, 15, 16, 17, 19
<223> OTHER INFORMATION: /mod_base = "2'-hydroxy corresponding base"

<400> SEQUENCE: 231
gcugucaucg aucaaagugt t                                          21
```

```
<210> SEQ ID NO 232
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 5, 7, 8, 11, 12, 17, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 6, 9, 10, 13, 14, 15, 16, 18
<223> OTHER INFORMATION: /mod_base = "2'-hydroxy corresponding base"

<400> SEQUENCE: 232
cugucaucga ucaaagugut t                                              21

<210> SEQ ID NO 233
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 5, 6, 9, 10, 15, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 4, 7, 8, 11, 12, 13, 14, 16, 18, 19
<223> OTHER INFORMATION: /mod_base = "2'-hydroxy corresponding base"

<400> SEQUENCE: 233
gucaucgauc aaaguguggt t                                              21

<210> SEQ ID NO 234
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 10, 13, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 4, 5, 6, 7, 8, 9, 11, 12, 14, 15, 17, 18, 19
<223> OTHER INFORMATION: /mod_base = "2'-hydroxy corresponding base"

<400> SEQUENCE: 234
uuugaucgau gacagcagct t                                              21
```

```
<210> SEQ ID NO 235
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 6, 13, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 5, 7, 8, 9, 10, 11, 12, 14, 15, 16, 18, 19
<223> OTHER INFORMATION: /mod_base = "2'-hydroxy corresponding base"

<400> SEQUENCE: 235
caucgugccg ucugucuggt t                                             21

<210> SEQ ID NO 236
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 5, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 6, 7, 8, 9, 10, 11, 12, 13, 14, 15, 16, 18, 19
<223> OTHER INFORMATION: /mod_base = "2'-hydroxy corresponding base"

<400> SEQUENCE: 236
uggguguCuc gccuccuuct t                                             21

<210> SEQ ID NO 237
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 6, 9, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 7, 8, 10, 11, 12, 13, 14, 16, 17, 19
<223> OTHER INFORMATION: /mod_base = "2'-hydroxy corresponding base"

<400> SEQUENCE: 237
```

```
guagguucua cgucuugcat t                                      21
```

<210> SEQ ID NO 238
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 6, 9, 10, 11, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 7, 8, 12, 13, 14, 15, 16, 17, 19
<223> OTHER INFORMATION: /mod_base = "2'-hydroxy corresponding base"

<400> SEQUENCE: 238

```
ucccacacuu ugaucgaugt t                                      21
```

<210> SEQ ID NO 239
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 7, 14, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 4, 5, 6, 8, 9, 10, 11, 12, 13, 15, 16, 17, 19
<223> OTHER INFORMATION: /mod_base = "2'-hydroxy corresponding base"

<400> SEQUENCE: 239

```
ccaucgugcc gucugucugt t                                      21
```

<210> SEQ ID NO 240
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 6, 10
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 7, 8, 9, 11, 12, 13, 14, 15, 16, 17, 18,
      19
<223> OTHER INFORMATION: /mod_base = "2'-hydroxy corresponding base"

```
<400> SEQUENCE: 240
ggaagugggu gucucgccut t                                              21

<210> SEQ ID NO 241
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 5, 8, 14, 15, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 4, 6, 7, 9, 10, 11, 12, 13, 16, 18, 19
<223> OTHER INFORMATION: /mod_base = "2'-hydroxy corresponding base"

<400> SEQUENCE: 241
uagguucuac gcuugcagt t                                               21

<210> SEQ ID NO 242
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 7, 10, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 5, 6, 8, 9, 11, 12, 13, 14, 16, 17, 18, 19
<223> OTHER INFORMATION: /mod_base = "2'-hydroxy corresponding base"

<400> SEQUENCE: 242
gcucagugcc aucgugccgt t                                              21

<210> SEQ ID NO 243
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 5, 12, 15, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 6, 7, 8, 9, 10, 11, 13, 14, 16, 17, 19
<223> OTHER INFORMATION: /mod_base = "2'-hydroxy corresponding base"
```

<400> SEQUENCE: 243
acuuugaucg augacagcat t          21

<210> SEQ ID NO 244
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 6, 13, 15, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 4, 5, 7, 8, 9, 10, 11, 12, 14, 16, 18, 19
<223> OTHER INFORMATION: /mod_base = "2'-hydroxy corresponding base"

<400> SEQUENCE: 244
uauuccaaga ccuauguuct t          21

<210> SEQ ID NO 245
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 9, 12, 15
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 3, 4, 5, 6, 7, 8, 10, 11, 13, 14, 16, 17, 18, 19
<223> OTHER INFORMATION: /mod_base = "2'-hydroxy corresponding base"

<400> SEQUENCE: 245
uugaucgaug acagcagcct t          21

<210> SEQ ID NO 246
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 4, 11, 14, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 5, 6, 7, 8, 9, 10, 12, 13, 15, 16, 18, 19

-continued

<223> OTHER INFORMATION: /mod_base = "2'-hydroxy corresponding base"

<400> SEQUENCE: 246
cuuugaucga ugacagcagt t                                          21

<210> SEQ ID NO 247
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 7, 10, 13
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 2, 3, 4, 5, 6, 8, 9, 11, 12, 14, 15, 16, 17, 18, 19
<223> OTHER INFORMATION: /mod_base = "2'-hydroxy corresponding base"

<400> SEQUENCE: 247
gaucgaugac agcagccgct t                                          21

<210> SEQ ID NO 248
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 5, 6, 13, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 2, 3, 7, 8, 9, 10, 11, 12, 14, 15, 17, 18, 19
<223> OTHER INFORMATION: /mod_base = "2'-hydroxy corresponding base"

<400> SEQUENCE: 248
cacuuugauc gaugacagct t                                          21

<210> SEQ ID NO 249
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 5, 6, 7, 14, 17
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base

```
<222> LOCATION: 1, 3, 4, 8, 9, 10, 11, 12, 13, 15, 16, 18, 19
<223> OTHER INFORMATION: /mod_base = "2'-hydroxy corresponding base"

<400> SEQUENCE: 249
acacuuugau cgaugacagt t                                              21

<210> SEQ ID NO 250
<211> LENGTH: 21
<212> TYPE: DNA
<213> ORGANISM: Artificial sequence
<220> FEATURE:
<223> OTHER INFORMATION: siRNAs targeting hamp
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 4, 7, 8, 9, 16
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "5'-thio thymidine"
<220> FEATURE:
<221> NAME/KEY: modified_base
<222> LOCATION: 1, 3, 5, 6, 10, 11, 12, 13, 14, 15, 17, 18, 19
<223> OTHER INFORMATION: /mod_base = "2'-hydroxy corresponding base"

<400> SEQUENCE: 250
ccacacuuug aucgaugact t                                              21
```